US008597658B2

(12) United States Patent
Quinnan et al.

(10) Patent No.: US 8,597,658 B2
(45) Date of Patent: Dec. 3, 2013

(54) HIV-1 ENVELOPE GLYCOPROTEIN OLIGOMER AND METHODS OF USE

(75) Inventors: Gerald Quinnan, Rockville, MD (US); Christopher Broder, Silver Spring, MD (US)

(73) Assignee: The Henry M. Jackson Foundation for the Advancement of Military Medicine, Inc., Bethesda, MD (US)

( * ) Notice: Subject to any disclaimer, the term of this patent is extended or adjusted under 35 U.S.C. 154(b) by 515 days.

(21) Appl. No.: 12/742,272

(22) PCT Filed: Nov. 12, 2008

(86) PCT No.: PCT/US2008/083190
§ 371 (c)(1), (2), (4) Date: Aug. 24, 2010

(87) PCT Pub. No.: WO2009/102357
PCT Pub. Date: Aug. 20, 2009

(65) Prior Publication Data

US 2010/0316661 A1 Dec. 16, 2010

Related U.S. Application Data

(60) Provisional application No. 60/987,287, filed on Nov. 12, 2007.

(51) Int. Cl.
*A61K 39/00* (2006.01)
*A61K 39/21* (2006.01)
*C07K 14/00* (2006.01)

(52) U.S. Cl.
USPC ...................... 424/188.1; 424/192.1; 530/395

(58) Field of Classification Search
None
See application file for complete search history.

(56) References Cited

U.S. PATENT DOCUMENTS

| | | | | |
|---|---|---|---|---|
| 5,292,646 | A * | 3/1994 | McCoy et al. | 435/69.7 |
| 6,039,957 | A | 3/2000 | Earl et al. | |
| 2005/0106160 | A1 | 5/2005 | Dimitrov et al. | |

OTHER PUBLICATIONS

Quinnan et al., AIDS Research and Human Retroviruses, 1999, 15(6): 561-570.*
Yang et al., Journal of Virology, 2002, 76(9):4634-4642.*
Huang et al., J. Biochem. Biophys. Methods, 2006.*
Zhang, et al., "Extensively Cross-Reactive Anti-HIV-1 Neutralizing Antibodies Induced by gp 140 Immunization", PNAS, 104, pp. 10193-10198, 2007.
Yang, et al., "A Trimeric HIV-1 Fusion Peptide Construct Which Does Not Self-Associate in Aqueous Solution . . . ", J Am Chem Soc., 126, pp. 14722-14723, 2004.
International Search Report of PCT/US2008/083190.

* cited by examiner

*Primary Examiner* — Nicole Kinsey White
(74) *Attorney, Agent, or Firm* — Morgan, Lewis & Bockius LLP

(57) ABSTRACT

This invention relates to fusion polypeptides comprised of a trimerization domain fused to a non-membrane bound, non-cleaved gp160 polypeptide derived from the R2 HIV-1 Env glycoprotein and to compositions comprising the fusion polypeptides. This invention further relates to oligomers of the fusion polypeptides. This invention also relates to nucleic acids encoding the fusion polypeptides. This invention also relates to diagnostic and therapeutic methods using the fusion polypeptides. Further, this invention relates to the induction of cross-reactive neutralizing antibodies against HIV-1, and to immunogenic compositions for the prevention and treatment of infection by HIV-1.

11 Claims, 11 Drawing Sheets

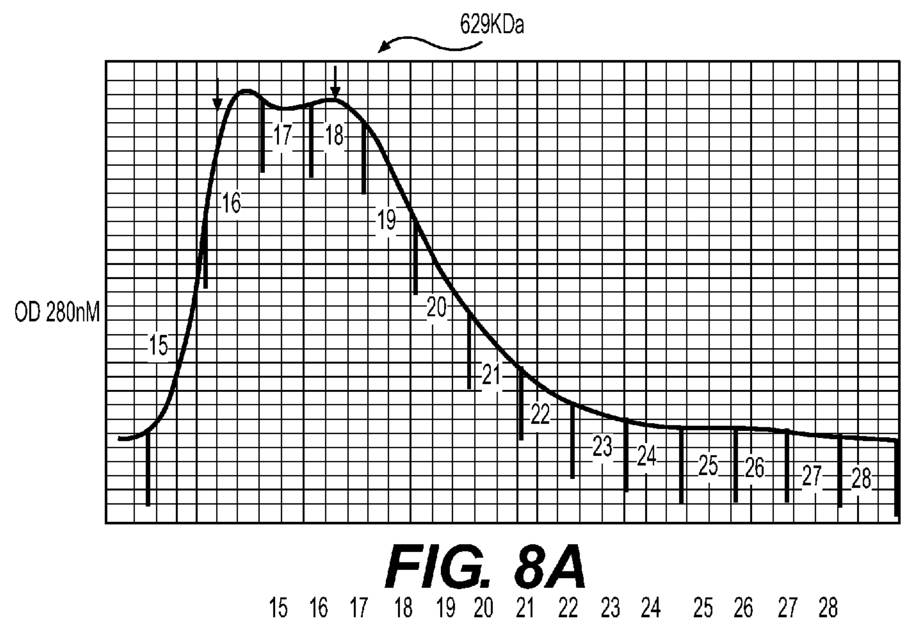
FIG. 8A
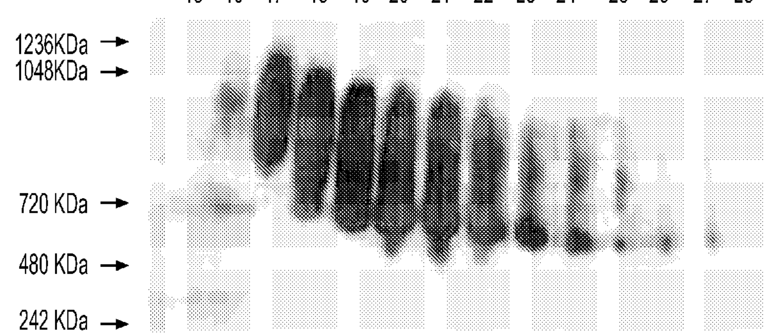
FIG. 8B
15 16 17 18 19 20 21 22 23 24 25 26 27
1236KDa →
1034KDa →
720 KDa →
480 KDa →
242 KDa →
FIG. 8C

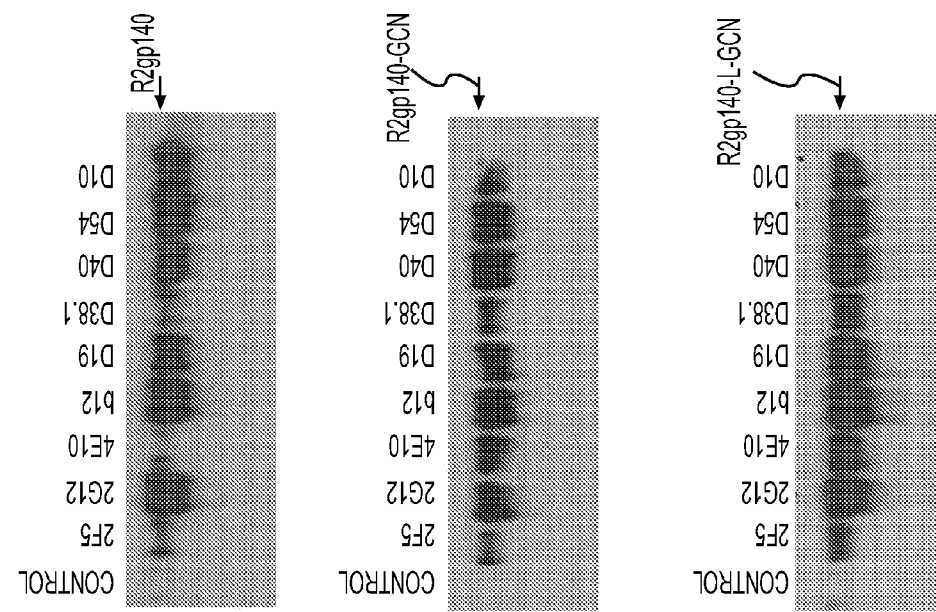
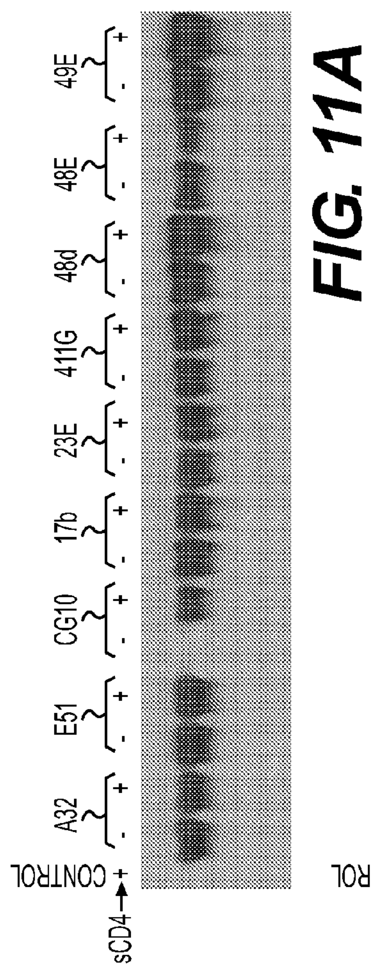
FIG. 11A
FIG. 11B
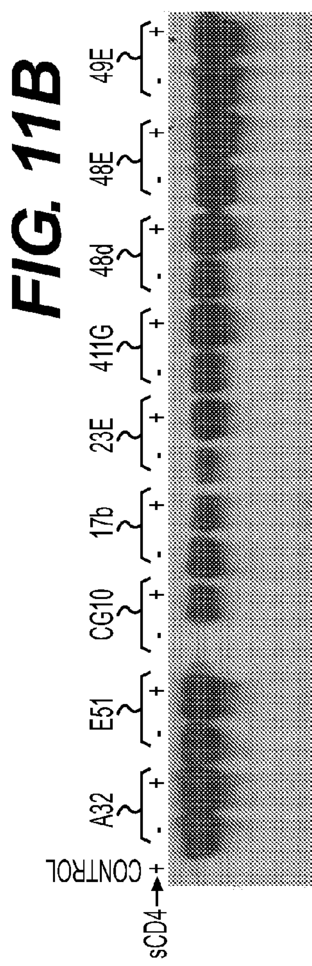
FIG. 11C

```
                          SEQUENCE LISTING

<160> NUMBER OF SEQ ID NOS: 8

<210> SEQ ID NO 1
<211> LENGTH: 2079
<212> TYPE: DNA
<213> ORGANISM: Human immunodeficiency virus

<400> SEQUENCE: 1

atgcgcgtga aggggatccg ccgcaactac cagcactggt ggggctgggg caccatgctg     60

ctgggcctgc tgatgatctg cagcgccacc gagaagctgt gggtgaccgt gtactacggc    120

gtgcccgtgt ggaaggaggc caccaccacc ctgttctgcg ccagcgacgc caaggcctac    180

gacaccgagg cccacaacgt gtgggccacc cacgcctgcg tgcccaccga ccccaacccc    240

caggaggtgg agctggtgaa cgtgaccgag aacttcaaca tgtggaagaa caacatggtg    300

gagcagatgc acgaggacat catcagcctg tgggaccaga gcctgaagcc ctgcgtgaag    360

ctgacccccc tgtgcgtgac cctgaactgc accgacctgc gcaacaccac caacaccaac    420

aacagcaccg acaacaacaa cagcaacagc gagggcacca tcaagggcgg cgagatgaag    480

aactgcagct tcaacatcgc cacctccatc ggcgacaaga tgcagaagga gtacgccctg    540

ctgtacaagc tggacatcga gcccatcgac aacgacaaca ccagctaccg cctgatcagc    600

tgcaacacca gcgtgatcac ccaggcctgc cccaagatca gcttcgagcc catccccatc    660

cactactgcg cccccgccgg cttcgccatc ctgaagtgca acgacaagaa gttcagcggc    720

aagggcagct gcaagaacgt gagcaccgtg cagtgcaccc acggcatccg ccccgtggtg    780

agcacccagc tgctgctgaa cggcagcctg gccgaggagg aggtggtgat ccgcagcgag    840

aacttcacca acaacgccaa gaccatcatc gtgcagctgc gcgagcccgt gaagatcaac    900

tgcagccgcc ccaacaacaa cacccgcaag agcatcccca tgggccccgg ccgcgccttc    960

tacaccaccg gccagatcat cggcgacatc cgccaggccc actgcaacat cagcaagacc   1020

aactggacca acgccctgaa gcaggtggtg gagaagctgg gcgagcagtt caacaagacc   1080

aagatcgtgt tcaccaacag cagcggcggc gacccggaga tcgtgaccca cagcttcaac   1140

tgcgccggcg agttcttcta ctgcaacacc acccagctgt tcgacagcat ctggaacagc   1200

gagaacggca cctggaacat cacccgcggc ctgaacaaca ccggccgcaa cgacaccatc   1260

accctgccct gccgcatcaa gcagatcatc aaccgctggc aggaagtggg caaggccatg   1320

tacgcccctc ccatcaaggg caacatcagc tgcagcagca acatcaccgg cctgctgctg   1380

acccgcgacg gcggcaagga cgacaacagc cgcgacggca acgagacctt ccgccccggc   1440

ggcggcgaca tgcgcgacaa ctggcgcagc gagctgtaca agtacaaggt ggtgaagatc   1500

gagcccctgg gcgtggcccc caccaaggcc aagcgacgcg tggtgcagag cgaggagagc   1560

gctgtgggcc tgggcgctat gttcatcggc ttcctgggcg ctgctggcag caccatgggc   1620

gctgctagcg tgaccctgac cgtgcaggct cggcagctgc tcagcggcat cgtgcagcag   1680
```

```
cagagcaacc tgctccgggc tatcgaagcc cagcagcacc tgctgcagct caccgtgtgg   1740

ggcatcaaac agctgcaggc tcggatcctg gctgtggagc ggtacctgaa agatcagcag   1800

ctgctcggca tctggggctg cagcggcaaa ctgatctgca ccaccaccgt gccctggaac   1860

gccagctgga gcaagaacaa gaccctggag gccatctgga acaacatgac ctggatgcag   1920

tgggacaagg agatcgacaa ctacaccagc ctgatctaca gcctgatcga ggaaagccag   1980

atccagcagg agaagaacga acaggaactg ctggagctgg acaagtgggc caacctgtgg   2040

aactggttcg acatcagcaa ctggctgtgg tacatcaag                          2079


<210> SEQ ID NO 2
<211> LENGTH: 693
<212> TYPE: PRT
<213> ORGANISM: Human immunodeficiency virus

<400> SEQUENCE: 2

Met Arg Val Lys Gly Ile Arg Arg Asn Tyr Gln His Trp Trp Gly Trp
1               5                   10                  15

Gly Thr Met Leu Leu Gly Leu Leu Met Ile Cys Ser Ala Thr Glu Lys
            20                  25                  30

Leu Trp Val Thr Val Tyr Tyr Gly Val Pro Val Trp Lys Glu Ala Thr
        35                  40                  45

Thr Thr Leu Phe Cys Ala Ser Asp Ala Lys Ala Tyr Asp Thr Glu Ala
    50                  55                  60

His Asn Val Trp Ala Thr His Ala Cys Val Pro Thr Asp Pro Asn Pro
65                  70                  75                  80

Gln Glu Val Glu Leu Val Asn Val Thr Glu Asn Phe Asn Met Trp Lys
                85                  90                  95

Asn Asn Met Val Glu Gln Met His Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

Asn Cys Thr Asp Leu Arg Asn Thr Thr Asn Thr Asn Asn Ser Thr Asp
    130                 135                 140

Asn Asn Asn Ser Asn Ser Glu Gly Thr Ile Lys Gly Gly Glu Met Lys
145                 150                 155                 160

Asn Cys Ser Phe Asn Ile Ala Thr Ser Ile Gly Asp Lys Met Gln Lys
                165                 170                 175

Glu Tyr Ala Leu Leu Tyr Lys Leu Asp Ile Glu Pro Ile Asp Asn Asp
            180                 185                 190

Asn Thr Ser Tyr Arg Leu Ile Ser Cys Asn Thr Ser Val Ile Thr Gln
        195                 200                 205

Ala Cys Pro Lys Ile Ser Phe Glu Pro Ile Pro Ile His Tyr Cys Ala
    210                 215                 220

Pro Ala Gly Phe Ala Ile Leu Lys Cys Asn Asp Lys Lys Phe Ser Gly
225                 230                 235                 240

Lys Gly Ser Cys Lys Asn Val Ser Thr Val Gln Cys Thr His Gly Ile
                245                 250                 255

Arg Pro Val Val Ser Thr Gln Leu Leu Leu Asn Gly Ser Leu Ala Glu
            260                 265                 270

Glu Glu Val Val Ile Arg Ser Glu Asn Phe Thr Asn Asn Ala Lys Thr
        275                 280                 285

Ile Ile Val Gln Leu Arg Glu Pro Val Lys Ile Asn Cys Ser Arg Pro
    290                 295                 300
```

```
Asn Asn Asn Thr Arg Lys Ser Ile Pro Met Gly Pro Gly Arg Ala Phe
305                 310                 315                 320

Tyr Thr Thr Gly Gln Ile Ile Gly Asp Ile Arg Gln Ala His Cys Asn
                325                 330                 335

Ile Ser Lys Thr Asn Trp Thr Asn Ala Leu Lys Gln Val Val Glu Lys
            340                 345                 350

Leu Gly Glu Gln Phe Asn Lys Thr Lys Ile Val Phe Thr Asn Ser Ser
        355                 360                 365

Gly Gly Asp Pro Glu Ile Val Thr His Ser Phe Asn Cys Ala Gly Glu
    370                 375                 380

Phe Phe Tyr Cys Asn Thr Thr Gln Leu Phe Asp Ser Ile Trp Asn Ser
385                 390                 395                 400

Glu Asn Gly Thr Trp Asn Ile Thr Arg Gly Leu Asn Asn Thr Gly Arg
                405                 410                 415

Asn Asp Thr Ile Thr Leu Pro Cys Arg Ile Lys Gln Ile Ile Asn Arg
            420                 425                 430

Trp Gln Glu Val Gly Lys Ala Met Tyr Ala Pro Pro Ile Lys Gly Asn
        435                 440                 445

Ile Ser Cys Ser Ser Asn Ile Thr Gly Leu Leu Leu Thr Arg Asp Gly
    450                 455                 460

Gly Lys Asp Asp Asn Ser Arg Asp Gly Asn Glu Thr Phe Arg Pro Gly
465                 470                 475                 480

Gly Gly Asp Met Arg Asp Asn Trp Arg Ser Glu Leu Tyr Lys Tyr Lys
                485                 490                 495

Val Val Lys Ile Glu Pro Leu Gly Val Ala Pro Thr Lys Ala Lys Arg
            500                 505                 510

Arg Val Val Gln Ser Glu Glu Ser Ala Val Gly Leu Gly Ala Met Phe
        515                 520                 525

Ile Gly Phe Leu Gly Ala Ala Gly Ser Thr Met Gly Ala Ala Ser Val
    530                 535                 540

Thr Leu Thr Val Gln Ala Arg Gln Leu Leu Ser Gly Ile Val Gln Gln
545                 550                 555                 560

Gln Ser Asn Leu Leu Arg Ala Ile Glu Ala Gln Gln His Leu Leu Gln
                565                 570                 575

Leu Thr Val Trp Gly Ile Lys Gln Leu Gln Ala Arg Ile Leu Ala Val
            580                 585                 590

Glu Arg Tyr Leu Lys Asp Gln Gln Leu Leu Gly Ile Trp Gly Cys Ser
        595                 600                 605

Gly Lys Leu Ile Cys Thr Thr Thr Val Pro Trp Asn Ala Ser Trp Ser
    610                 615                 620

Lys Asn Lys Thr Leu Glu Ala Ile Trp Asn Asn Met Thr Trp Met Gln
625                 630                 635                 640

Trp Asp Lys Glu Ile Asp Asn Tyr Thr Ser Leu Ile Tyr Ser Leu Ile
                645                 650                 655

Glu Glu Ser Gln Ile Gln Gln Glu Lys Asn Glu Gln Glu Leu Leu Glu
            660                 665                 670

Leu Asp Lys Trp Ala Asn Leu Trp Asn Trp Phe Asp Ile Ser Asn Trp
        675                 680                 685

Leu Trp Tyr Ile Lys
    690
```

<210> SEQ ID NO 3
<211> LENGTH: 2214
<212> TYPE: DNA
<213> ORGANISM: Artificial

<220> FEATURE:
<223> OTHER INFORMATION: Fusion of truncated HIV with GCN4 coiled coil

<400> SEQUENCE: 3

```
atgcgcgtga aggggatccg ccgcaactac cagcactggt ggggctgggg caccatgctg     60
ctgggcctgc tgatgatctg cagcgccacc gagaagctgt gggtgaccgt gtactacggc    120
gtgcccgtgt ggaaggaggc caccaccacc ctgttctgcg ccagcgacgc caaggcctac    180
gacaccgagg cccacaacgt gtgggccacc cacgcctgcg tgcccaccga ccccaacccc    240
caggaggtgg agctggtgaa cgtgaccgag aacttcaaca tgtggaagaa caacatggtg    300
gagcagatgc acgaggacat catcagcctg tgggaccaga gcctgaagcc ctgcgtgaag    360
ctgacccccc tgtgcgtgac cctgaactgc accgacctgc gcaacaccac caacaccaac    420
aacagcaccg acaacaacaa cagcaacagc gagggcacca tcaagggcgg cgagatgaag    480
aactgcagct tcaacatcgc cacctccatc ggcgacaaga tgcagaagga gtacgccctg    540
ctgtacaagc tggacatcga gcccatcgac aacgacaaca ccagctaccg cctgatcagc    600
tgcaacacca gcgtgatcac ccaggcctgc cccaagatca gcttcgagcc catccccatc    660
cactactgcg cccccgccgg cttcgccatc ctgaagtgca acgacaagaa gttcagcggc    720
aagggcagct gcaagaacgt gagcaccgtg cagtgcaccc acggcatccg ccccgtggtg    780
agcacccagc tgctgctgaa cggcagcctg gccgaggagg aggtggtgat ccgcagcgag    840
aacttcacca acaacgccaa gaccatcatc gtgcagctgc gcgagcccgt gaagatcaac    900
tgcagccgcc ccaacaacaa cacccgcaag agcatcccca tgggccccgg ccgcgccttc    960
tacaccaccg gccagatcat cggcgacatc cgccaggccc actgcaacat cagcaagacc   1020
aactggacca acgccctgaa gcaggtggtg gagaagctgg gcgagcagtt caacaagacc   1080
aagatcgtgt tcaccaacag cagcggcggc gacccggaga tcgtgaccca cagcttcaac   1140
tgcgccggcg agttcttcta ctgcaacacc acccagctgt tcgacagcat ctggaacagc   1200
gagaacggca cctggaacat cacccgcggc ctgaacaaca ccggccgcaa cgacaccatc   1260
accctgccct gccgcatcaa gcagatcatc aaccgctggc aggaagtggg caaggccatg   1320
tacgcccctc ccatcaaggg caacatcagc tgcagcagca acatcaccgg cctgctgctg   1380
acccgcgacg gcggcaagga cgacaacagc cgcgacggca acgagacctt ccgccccggc   1440
ggcggcgaca tgcgcgacaa ctggcgcagc gagctgtaca agtacaaggt ggtgaagatc   1500
gagcccctgg gcgtggcccc caccaaggcc aagcgacgcg tggtgcagag cgaggagagc   1560
gctgtgggcc tgggcgctat gttcatcggc ttcctgggcg ctgctggcag caccatgggc   1620
gctgctagcg tgaccctgac cgtgcaggct cggcagctgc tcagcggcat cgtgcagcag   1680
cagagcaacc tgctccgggc tatcgaagcc cagcagcacc tgctgcagct caccgtgtgg   1740
ggcatcaaac agctgcaggc tcggatcctg gctgtggagc ggtacctgaa agatcagcag   1800
ctgctcggca tctggggctg cagcggcaaa ctgatctgca ccaccaccgt gccctggaac   1860
gccagctgga gcaagaacaa gaccctggag gccatctgga acaacatgac ctggatgcag   1920
tgggacaagg agatcgacaa ctacaccagc ctgatctaca gcctgatcga ggaaagccag   1980
atccagcagg agaagaacga acaggaactg ctggagctgg acaagtgggc caacctgtgg   2040
aactggttcg acatcagcaa ctggctgtgg tacatcaaga agcttatgaa gcagatcgag   2100
gacaagatcg aggagatcct gagcaagatc taccacatcg agaacgagat cgccaggatc   2160
aagaagctga tcggcgaggc ccctggcggc atcgagggca ggaagcttta ataa         2214
```

<210> SEQ ID NO 4
<211> LENGTH: 736
<212> TYPE: PRT
<213> ORGANISM: Artificial
<220> FEATURE:
<223> OTHER INFORMATION: Fusion of truncated HIV with GCN4 coiled coil

<400> SEQUENCE: 4

```
Met Arg Val Lys Gly Ile Arg Arg Asn Tyr Gln His Trp Trp Gly Trp
1               5                   10                  15

Gly Thr Met Leu Leu Gly Leu Leu Met Ile Cys Ser Ala Thr Glu Lys
            20                  25                  30

Leu Trp Val Thr Val Tyr Tyr Gly Val Pro Val Trp Lys Glu Ala Thr
        35                  40                  45

Thr Thr Leu Phe Cys Ala Ser Asp Ala Lys Ala Tyr Asp Thr Glu Ala
    50                  55                  60

His Asn Val Trp Ala Thr His Ala Cys Val Pro Thr Asp Pro Asn Pro
65                  70                  75                  80

Gln Glu Val Glu Leu Val Asn Val Thr Glu Asn Phe Asn Met Trp Lys
                85                  90                  95

Asn Asn Met Val Glu Gln Met His Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

Asn Cys Thr Asp Leu Arg Asn Thr Thr Asn Thr Asn Asn Ser Thr Asp
    130                 135                 140

Asn Asn Asn Ser Asn Ser Glu Gly Thr Ile Lys Gly Gly Glu Met Lys
145                 150                 155                 160

Asn Cys Ser Phe Asn Ile Ala Thr Ser Ile Gly Asp Lys Met Gln Lys
                165                 170                 175

Glu Tyr Ala Leu Leu Tyr Lys Leu Asp Ile Glu Pro Ile Asp Asn Asp
            180                 185                 190

Asn Thr Ser Tyr Arg Leu Ile Ser Cys Asn Thr Ser Val Ile Thr Gln
        195                 200                 205

Ala Cys Pro Lys Ile Ser Phe Glu Pro Ile Pro Ile His Tyr Cys Ala
    210                 215                 220

Pro Ala Gly Phe Ala Ile Leu Lys Cys Asn Asp Lys Lys Phe Ser Gly
225                 230                 235                 240

Lys Gly Ser Cys Lys Asn Val Ser Thr Val Gln Cys Thr His Gly Ile
                245                 250                 255

Arg Pro Val Val Ser Thr Gln Leu Leu Leu Asn Gly Ser Leu Ala Glu
            260                 265                 270

Glu Glu Val Val Ile Arg Ser Glu Asn Phe Thr Asn Asn Ala Lys Thr
        275                 280                 285

Ile Ile Val Gln Leu Arg Glu Pro Val Lys Ile Asn Cys Ser Arg Pro
    290                 295                 300

Asn Asn Asn Thr Arg Lys Ser Ile Pro Met Gly Pro Gly Arg Ala Phe
305                 310                 315                 320

Tyr Thr Thr Gly Gln Ile Ile Gly Asp Ile Arg Gln Ala His Cys Asn
                325                 330                 335

Ile Ser Lys Thr Asn Trp Thr Asn Ala Leu Lys Gln Val Val Glu Lys
            340                 345                 350

Leu Gly Glu Gln Phe Asn Lys Thr Lys Ile Val Phe Thr Asn Ser Ser
        355                 360                 365

Gly Gly Asp Pro Glu Ile Val Thr His Ser Phe Asn Cys Ala Gly Glu
    370                 375                 380
```

```
Phe Phe Tyr Cys Asn Thr Thr Gln Leu Phe Asp Ser Ile Trp Asn Ser
385                 390                 395                 400

Glu Asn Gly Thr Trp Asn Ile Thr Arg Gly Leu Asn Asn Thr Gly Arg
                405                 410                 415

Asn Asp Thr Ile Thr Leu Pro Cys Arg Ile Lys Gln Ile Ile Asn Arg
            420                 425                 430

Trp Gln Glu Val Gly Lys Ala Met Tyr Ala Pro Pro Ile Lys Gly Asn
        435                 440                 445

Ile Ser Cys Ser Ser Asn Ile Thr Gly Leu Leu Leu Thr Arg Asp Gly
    450                 455                 460

Gly Lys Asp Asp Asn Ser Arg Asp Gly Asn Glu Thr Phe Arg Pro Gly
465                 470                 475                 480

Gly Gly Asp Met Arg Asp Asn Trp Arg Ser Glu Leu Tyr Lys Tyr Lys
                485                 490                 495

Val Val Lys Ile Glu Pro Leu Gly Val Ala Pro Thr Lys Ala Lys Arg
            500                 505                 510

Arg Val Val Gln Ser Glu Glu Ser Ala Val Gly Leu Gly Ala Met Phe
        515                 520                 525

Ile Gly Phe Leu Gly Ala Ala Gly Ser Thr Met Gly Ala Ala Ser Val
    530                 535                 540

Thr Leu Thr Val Gln Ala Arg Gln Leu Leu Ser Gly Ile Val Gln Gln
545                 550                 555                 560

Gln Ser Asn Leu Leu Arg Ala Ile Glu Ala Gln Gln His Leu Leu Gln
                565                 570                 575

Leu Thr Val Trp Gly Ile Lys Gln Leu Gln Ala Arg Ile Leu Ala Val
            580                 585                 590

Glu Arg Tyr Leu Lys Asp Gln Gln Leu Leu Gly Ile Trp Gly Cys Ser
        595                 600                 605

Gly Lys Leu Ile Cys Thr Thr Thr Val Pro Trp Asn Ala Ser Trp Ser
    610                 615                 620

Lys Asn Lys Thr Leu Glu Ala Ile Trp Asn Asn Met Thr Trp Met Gln
625                 630                 635                 640

Trp Asp Lys Glu Ile Asp Asn Tyr Thr Ser Leu Ile Tyr Ser Leu Ile
                645                 650                 655

Glu Glu Ser Gln Ile Gln Gln Glu Lys Asn Glu Gln Glu Leu Leu Glu
            660                 665                 670

Leu Asp Lys Trp Ala Asn Leu Trp Asn Trp Phe Asp Ile Ser Asn Trp
        675                 680                 685

Leu Trp Tyr Ile Lys Lys Leu Met Lys Gln Ile Glu Asp Lys Ile Glu
    690                 695                 700

Glu Ile Leu Ser Lys Ile Tyr His Ile Glu Asn Glu Ile Ala Arg Ile
705                 710                 715                 720

Lys Lys Leu Ile Gly Glu Ala Pro Gly Gly Ile Glu Gly Arg Lys Leu
                725                 730                 735
```

<210> SEQ ID NO 5
<211> LENGTH: 123
<212> TYPE: DNA
<213> ORGANISM: Artificial
<220> FEATURE:
<223> OTHER INFORMATION: GCN4 coiled coil

<400> SEQUENCE: 5

```
atgaagcaga tcgaggacaa gatcgaggag atcctgagca agatctacca catcgagaac     60

gagatcgcca ggatcaagaa gctgatcggc gaggcccctg gcggcatcga gggcaggaag    120
```

-continued

```
ctt                                                                 123


<210> SEQ ID NO 6
<211> LENGTH: 41
<212> TYPE: PRT
<213> ORGANISM: Artificial
<220> FEATURE:
<223> OTHER INFORMATION: GCN4 coiled coil

<400> SEQUENCE: 6

Met Lys Gln Ile Glu Asp Lys Ile Glu Glu Ile Leu Ser Lys Ile Tyr
1               5                   10                  15

His Ile Glu Asn Glu Ile Ala Arg Ile Lys Lys Leu Ile Gly Glu Ala
            20                  25                  30

Pro Gly Gly Ile Glu Gly Arg Lys Leu
        35                  40


<210> SEQ ID NO 7
<211> LENGTH: 36
<212> TYPE: DNA
<213> ORGANISM: Artificial
<220> FEATURE:
<223> OTHER INFORMATION: Synthetic primer

<400> SEQUENCE: 7

ctgtggtaca tcaagaagct ttaataatct agaggg                              36


<210> SEQ ID NO 8
<211> LENGTH: 36
<212> TYPE: DNA
<213> ORGANISM: Artificial
<220> FEATURE:
<223> OTHER INFORMATION: Synthetic primer

<400> SEQUENCE: 8

ccctctagat tattaaagct tcttgatgta ccacag                              36
```

HIV-1 ENVELOPE GLYCOPROTEIN OLIGOMER AND METHODS OF USE

RELATED APPLICATIONS

The present application is a U.S. National Phase Application of International Application No. PCT/US2008/083190 (filed Nov. 12, 2008) which claims the benefit of U.S. Provisional Application No. 60/987,287 (filed Nov. 12, 2007), both of which are hereby incorporated by reference in their entireties.

ACKNOWLEDGEMENT OF FEDERAL SUPPORT

The present invention arose in part from research funded by the following federal grant monies: AI37438 and AI64070. The U.S. Government may have certain rights to the present invention.

SEQUENCE LISTING SUBMISSION VIA EFS-WEB

A computer readable text file, entitled "44508-5021-SeqListing.txt," created on or about May 10, 2010 with a file size of about 20 kb contains the sequence listing for this application and is hereby incorporated by reference in its entirety.

FIELD OF THE INVENTION

The present invention relates to a fusion polypeptide that is comprised by a first polypeptide that is a modified gp160 HIV-1 envelope protein derived from the donor of the Neutralizing Reference Human Serum (2) (R2) that cannot be proteolytically cleaved into the gp120 and gp41 subunits and that is truncated to avoid membrane anchoring and a second polypeptide that is a trimerization domain.

BACKGROUND OF THE INVENTION

Immunization to protect against Human Immunodeficiency Virus Type 1 (HIV-1) infections is a global priority. However, the efforts to develop an effective vaccine have been thus far unsuccessful in terms of protection of humans from acquisition of infection. The mechanism by which most viral vaccines protect against infection is through induction of antibodies that neutralize viral infectivity so that entry of the virus into cells of the vaccinated individual does not occur (Quinnan et al. (1997) Antiviral Agents and Human Viral Diseases, ed. Galasso, Whitley, and Merigan, Raven Press, pp. 791-834).

A major goal of efforts to develop a vaccine against HIV-1 is the induction of broadly cross-reactive neutralizing antibodies (Burton et al. (2004) Nat. Immunol. 5:233-236). Induction of antibodies that are highly potent and mediate neutralization of HIV-1 with broad cross-reactivity against epidemic strains has not yet been achieved.

The HIV-1 envelope glycoprotein complex (Env) is displayed on the surface of the virus and is the target of neutralizing antibodies. Two different proteins comprise the Env complex: gp120, the surface component, and gp41, the transmembrane component. Each Env complex is believed to consist of three copies of each of these two proteins in a trimer of heterodimers. The glycoproteins are initially produced during virus infection as a polyprotein, designated gp160. Cellular proteases cleave gp160 into the two subunits, gp120 and gp41, which remain non-covalently associated with each other in the Env complex.

The epitopes that are the targets of cross-reactive neutralizing antibodies are displayed on the surface of the trivalent complex, and they depend upon the quaternary structure of this complex.

Conformation-independent neutralization epitopes are located on both the surface, gp120, and transmembrane, gp41, components of the Env (Scanlan et al. (2002) J Virol 76, 7306-7321; Zwick et al. (2001) J Virol 75, 10892-10905; Wyatt et al. (1998) Nature 393, 705-711). There are also conformational epitopes associated with the heterotrimeric complex, some of which overlap receptor or co-receptor binding sites (Labrijn et al. (2003) J Virol 77, 10557-10565).

Among most HIV-1-infected patients, the degree of neutralizing antibody cross-reactivity that develops is limited, but there are occasional patients who develop extensively cross-reactive antibody responses (Zhang et al. (1999) J Virol 73, 5225-5230). One particular Env, designated R2 and derived from an HIV-1-infected individual, generated serum antibodies that exhibited extensive neutralizing cross-reactivity against many primary strains of HIV-1 of diverse virus subtypes (Dong et al. (2003) J Virol 77, 3119-3130; Zhang et al. (2002) J Virol 76, 644-655). R2 is also highly unusual as a naturally occurring HIV-1 Env in that it is be capable of mediating CD4-independent infection (U.S. Pat. No. 7,090, 848; Zhang et al. (2002) J Virol 76, 644-655) Immunogenicity studies conducted in small animals and nonhuman primates have demonstrated that R2 induces neutralizing antibodies against multiple HIV-1 strains (Dong et al. (2003) J Virol 77, 3119-3130; Quinnan et al. (2005) J Virol 79, 3358-3369). The neutralizing cross-reactivity observed in those studies was greater than that previously reported in studies of other envelope immunogens (Labrijn et al. (2003) J Virol 77, 10557-10565).

These results were a major breakthrough, since they were the first demonstration that such a response was even possible. However, the potency of the response was modest, and not likely to be sufficient to result in durable immunity in a high proportion of vaccinated individuals. Therefore, research to identify methods to enhance the potency of the neutralizing response is much needed.

Preparation of soluble protein, which can be administered in a vaccine, that presents the same quaternary structure as the native trimeric complex on the surface of the virus is difficult, since extraction of the protein from the surface of the virus or cells is likely to substantially alter its quaternary structure.

The production of Env as gp140 is one approach that has been previously used (Zhang et al. (2007) Proc. Natl. Acad. Sci. U.S.A. 104:10193-10198; Dong et al. (2003). J. Virol. 77:3119-3130; Quinnan. et al. (2005) J. Virol. 79:3358-3369; Earl et al. (2001) J. Virol. 75:645-653). Under this approach, gp140 is produced in cell culture as a recombinant protein. The gp140 is a modified gp160, whereby the gp160 coding sequence is altered so that the protein produced lacks the amino acids necessary for protease cleavage, and further lacks the segments of gp41 that normally are imbedded in the viral membrane (transmembrane or TM segment) or in the interior of the virus or cell (cytoplasmic tail, CT). Since the gp140 protein is truncated so that the TM and CT segments are lacking, it is secreted by producing cells, and can be purified from tissue culture medium using non-denaturing conditions. Thus, the purified protein is at least partially in a trimeric form that presents a quaternary structure that is similar to that of the native protein on intact virus.

A prior study to assess antibody production was conducted in three groups of rabbits, with each group receiving different immunogens (Zhang et al. (2007) Proc. Natl. Acad. Sci. U.S.A. 104:10193-10198). One group received HIV-1 envelope glycoprotein R2gp120 in the adjuvant AS02A, a second group received the HIV-1 envelope glycoprotein R2gp140 in the adjuvant AS02A, and a third group received just the adjuvant AS02A.

Rabbits that received R2gp120 immunization developed a reasonably rapid and potent neutralizing antibody response that had very limited cross-reactivity, while the rabbits that received R2gp140 developed broadly cross-reactive neutralization that developed more slowly, and was lower in potency, as demonstrated in FIG. 1. One explanation for this observed difference is that neutralizing antibodies induced by R2gp120 with restricted cross-reactivity may be directed against high affinity, immunodominant, strain-specific epitopes, whereas those neutralizing antibodies induced by R2gp140 with broad cross-reactivity may be directed against lower affinity, cross-reactive epitopes.

As the R2gp140 recombinant preparation is a mixture of monomeric, trimeric, and multimeric proteins, the immunodominant, high-affinity epitopes on some of the protein species in the mixture override the development of an immune response against the important epitopes. Antibody responses typically induced by proteins tend to develop with kinetics more similar to the R2gp120-induced response than the cross-reactive response induced by R2gp140. That is, a potent response is obtained after a single immunization in adjuvant, and a potent booster effect is observed if a booster immunization is given a month or more later. In this respect, the R2gp120-induced response is typical, while the cross-reactive neutralizing response induced by R2gp140 is atypical. This difference indicates that B cells that elaborate the antibodies mediating highly cross-reactive neutralization are less effectively induced than the B cells that produce antibodies mediating neutralization with limited cross-reactivity.

Recent data further attests to the existence of potentially important differences in antigenic structure of R2gp120 and R2gp140. These data regard testing of sera from the same rabbits for the presence of antibodies binding to HIV-1 Env of different strains, and testing of ability of synthetic peptides to block neutralizing activity. The results of testing of immunoglobulin (Ig) binding to Env of different strains were also previously reported (Zhang et al. (2007) Proc. Natl. Acad. Sci. U.S.A. 104:10193-10198). Ig binding to the strain R2 Env used for immunization, and two other strains of Env was determined by enzyme-linked immunosorbent assay (ELISA), as shown in FIG. 2. The antibodies induced by gp120 immunization reacted much more with R2gp140 than with the gp140s from either of two other strains. In contrast, the antibodies induced by R2gp140 immunization reacted similarly with all three gp140s. The induction of strain-specific antibodies by immunization with gp120 is well established in the published literature.

The failure of R2gp140 immunization to induce such antibodies is unexpected, and indicates that the epitopes that induce the strain specific response are not effectively presented to the immune system by R2gp140 even though the full R2gp120 sequence is included in the protein. Strain-specific responses tend to be directed toward variable parts of the protein, rather than those sequences that are conserved among strains. Notably, the immunodominant variable region epitope in R2gp120 is variable region 3 (V3). The intriguing possibility is that the conformation assumed by R2gp140 is such that the immunodominant, variable region 3 epitope may be masked so that it cannot be seen by the immune system. This possibility is consistent with the evidence that demonstrates that a major reason why anti-V3 antibodies display limited neutralizing cross-reactivity is that the conformation of Env on the surface of the virus masks access to the critical region of the V3 loop.

Prior studies were conducted to determine whether antibodies directed against the V1, V2, or V3 regions of Env contributed to the neutralizing response induced by R2gp120 or R2gp140. For these studies peptides were synthesized that corresponded to sequences of these regions. This approach was taken because previous studies had demonstrated that the neutralization by antibodies directed against these regions could be blocked by the presence of soluble peptides. V1 and V2 region peptides had no effect on neutralization by the sera from either the R2gp120 or R2gp140 immunized rabbits. Similarly, V1 and V2 region deletion mutants were as susceptible to neutralization by the rabbit sera as virus presenting wild-type Env. In contrast, synthetic peptide homologous to the V3 region of R2 Env significantly blocked neutralization by sera from the gp120, but not gp140-immunized rabbits, as shown in FIG. 3. The results indicate that neutralizing antibodies directed against V3 contribute to the neutralizing response to R2gp120 but not the highly cross-reactive response induced by R2gp140. These results are consistent with the indication that V3 masking occurs in R2gp140.

Competition between high and low affinity epitopes for induction of B cell responses is well documented in the immunology literature. In fact, the successful induction of antigen-specific responses depends upon the amplification of responses resulting from high affinity interaction of B cells with antigen through the recruitment of T helper cells, and the deletion of B cell subsets that interact weakly with the antigen through apoptosis. In this manner, only antibodies with high affinity that are unlikely to cross-react with other, unrelated antigens are induced.

Epitopes that are immunodominant are those that are more successful in the competitive environment of B cell response induction. The observation that antibodies that mediate neutralization with restricted cross-reactivity develop as more typical responses, and that antibodies that mediate broad cross-reactivity develop more slowly and with lower potency indicates that the epitopes inducing the former are immunodominant. Undoubtedly, there are dominant and non-dominant epitopes on R2gp140, and the sequences that form the dominant epitopes on R2gp120 are all present on R2gp140. However, there is a reasonable basis to hypothesize that these dominant epitopes are not presented to B cells effectively by conformationally intact trimeric Env.

Compelling evidence exists that antibodies that bind conformationally intact Env neutralize primary viruses cross-reactively. In contrast, antibodies that do not bind conformationally intact Env of any particular virus do not neutralize that virus. Conversely, an Env that cannot be recognized by an antibody molecule would not be competent to induce antibody production by a B cell expressing that molecule on its surface.

The comparative features of the immune responses induced by R2gp120 and R2gp140 indicate that the response induced by R2gp140 represents the additive effects of forms of the protein that resemble R2gp120 in immunogenicity and forms that are distinct from gp120 in that they present epitopes associated with highly cross-reactive neutralization. Further, the data indicate that the immunodominant epitopes may be effectively presented only by the gp120-like species, while the epitopes associated with broad neutralizing cross-reactivity are only presented on the oligomeric species. Thus, there is a need for an immunogen that is highly purified oligomer to selectively induce the highly cross-reactive neutralizing response. Such a purified oligomer is also of use to allow for the absence of competition from more dominant epitopes. A need exists for a purified oligomer to permit conversion of the cross-reactive response into a high potency, rapid antibody response.

SUMMARY OF THE INVENTION

The present invention provides a fusion polypeptide comprised of derivations of the R2160 that is capable of associating as an oligomer in high concentrations. The present invention further includes mutations to the R2 derived gp160, such that the endogenous cleavage site is mutated. The present invention also includes mutations to the R2 derived gp160, such that the protein is not anchored to the transmembrane. The present invention provides for a non-cleaved non-membrane bound derivation of the R2160, designated R2gp140 protein (SEQ ID NO: 2) and corresponding nucleotide sequence (SEQ ID NO: 1).

The present invention provides a fusion polypeptide comprised of R2gp140 fused to a trimerization domain. In some embodiments, the trimerization domain is a coiled coil. In preferred embodiments, the trimerization domain is a GCN4 motif amino acid sequence (SEQ ID NO: 6) and corresponding nucleotide sequence (SEQ ID NO: 5). In preferred embodiments, the R2gp140 is fused to a trimerization domain, more preferably a coiled coil, and even more preferably a GCN4 motif (SEQ ID NO: 4).

The present invention also provides for additional polypeptides such as sites for cleavage and/or affinity tags and/or epitope tags to be fused to the R2gp140-trimerization domain fusion polypeptide. In some embodiments, the invention provides for a linker sequence inserted between one or more of the polypeptides in the fusion polypeptide.

The present invention also provides for a nucleic acid comprised of a nucleic acid encoding the R2gp140 fused to a nucleic acid encoding the trimerization domain. In preferred embodiments, the nucleic acid molecule encodes for the R2gp140 fused to a GCN4 motif (SEQ ID NO: 3).

The present invention also provides for oligomers of the R2gp140 fused to a trimerization domain. In some embodiments, the oligomer is a trimer of three R2gp140-trimerization domain fused polypeptides. In preferred embodiments, the fusion polypeptide of the present invention associates as a trimer in high concentrations.

The present invention also provides for immunogenic compositions comprised of the R2gp140 polypeptide fused to a trimerization domain. In preferred embodiments, the immunogenic composition is comprised of an oligomer comprising the R2gp140-trimerization domain fusion polypeptide. In more preferred embodiments, the oligomer is a trimer, even more preferably a trimer of the R2gp140-trimerization domain polypeptide.

The present invention also provides for methods of generating antibodies in a subject comprising administering one or more of the proteins, polypeptides and nucleic acids of the present invention, in an amount sufficient to induce the production of the antibodies. In preferred embodiments, the methods produce a highly potent, rapid cross-neutralizing antibody response. The methods may be used for treatment of or for prevention of infection by HIV-1.

BRIEF DESCRIPTION OF THE DRAWINGS

FIG. 5A shows a diagrammatic picture of the R2gp140-GCN4 showing the mutations of arginine to serine residues to remove the cleavage site.

FIGS. 8A-8C show size exclusion chromatography analysis of R2gp140 with purified from 293T. 1.5 mg of protein was run on a calibrated Superdex 200 10/300 gel filtration column. 400 μl fractions were collected; the molecular weight was estimated from a calibrated curve (FIG. 8A). 1 μl of each fraction was analyzed by BN PAGE followed by western blotting. Rabbit anti gp140, R2143 antibody was used for immunodetection followed by HRP conjugated anti-rabbit antibody (FIG. 8B). 5 μl of each fraction was analyzed by BN PAGE stained with coomassie blue (FIG. 8C).

FIG. 11 shows the monoclonal antibody binding analysis (right panel) and reactivity to CD4i and CD4-gp140 complex specific mAbs (left panel) of purified R2 gp140 dimer (A), R2 gp140+GCN trimer (B), and R2 gp140+linker+GCN trimer (C). For the right panel, 1 μg of different versions of purified R2 gp140 was incubated with or without excess (3 μg) sCD4 in 700 μl of reaction buffer (PBS containing 0.5% Triton®X-100) at 4° C. for overnight, followed by 2 μg of the indicated mAb for an additional 4 h. For the left panel, 1 μg of different versions of purified R2 gp140 was incubated with the indicated mAbs in 700 μl of reaction buffer for 4 h at 4° C. In both cases, the complex were then precipitated with 50 μl of Protein G Sepharose (20% solution) for an additional 2 h at 4° C. The samples were washed three times with lysis buffer (0.1 M Tris-HCl, pH 8.0, 0.1M NaCl, 0.1% Triton®X-100). The precipitated complex was resuspended in SDS-PAGE sample buffer, boiled for 5 min and resolved on 4-12% Bis-Tris SDS-PAGE followed by western blotting. The blots were then probed with a polyclonal rabbit anti-gp140 antiserum.

DETAILED DESCRIPTION

Figure 1:
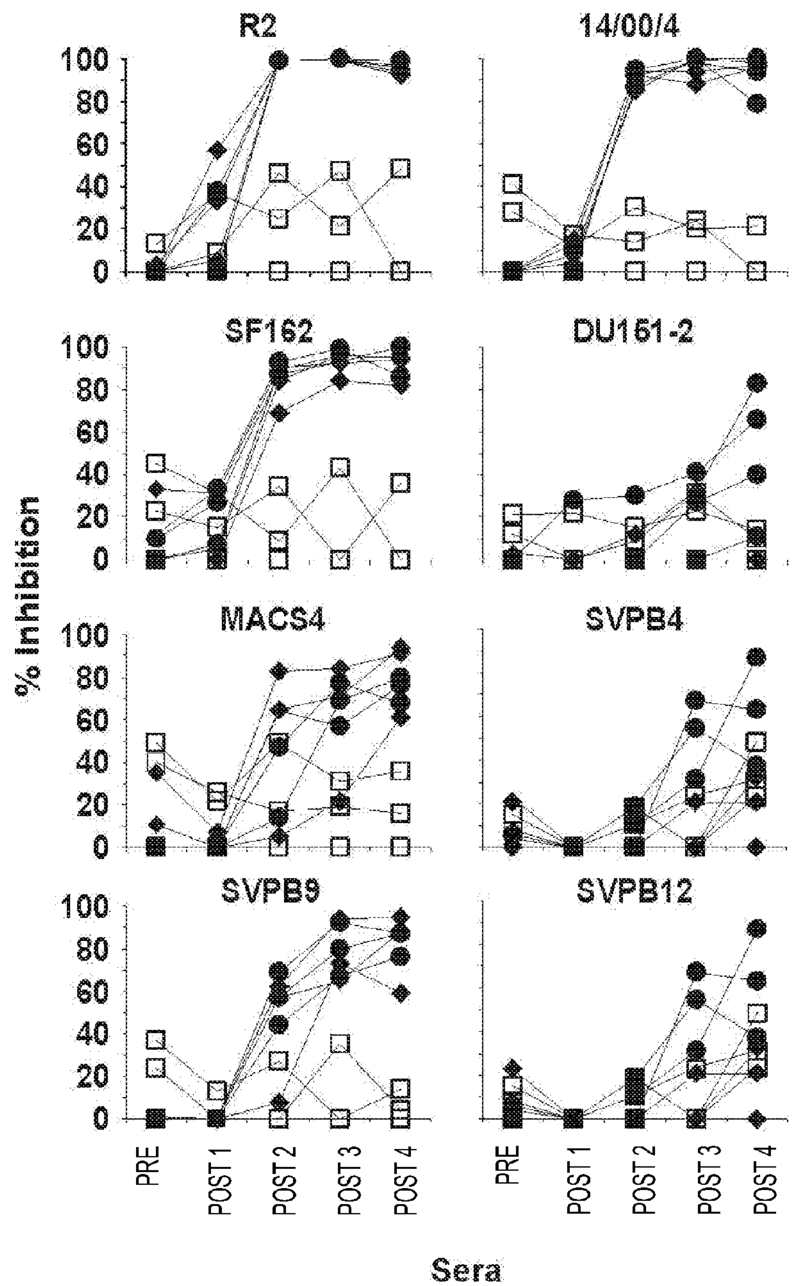
FIG. 1 shows the neutralization of HIV-1 strains by rabbit sera obtained after serial immunizations with R2gp120 (closed triangles), R2gp140 (closed circles), or adjuvant alone (open squares). The strains R2, SF162, MACS4, SVPB9, and 14/00/4 were neutralized by the gp120- and gp140-induced responses after two doses, while the strains DU151-2, SVPB4, and SVPB12 were only neutralized by the gp140-induced responses, and not until after four doses.
Figure 2:
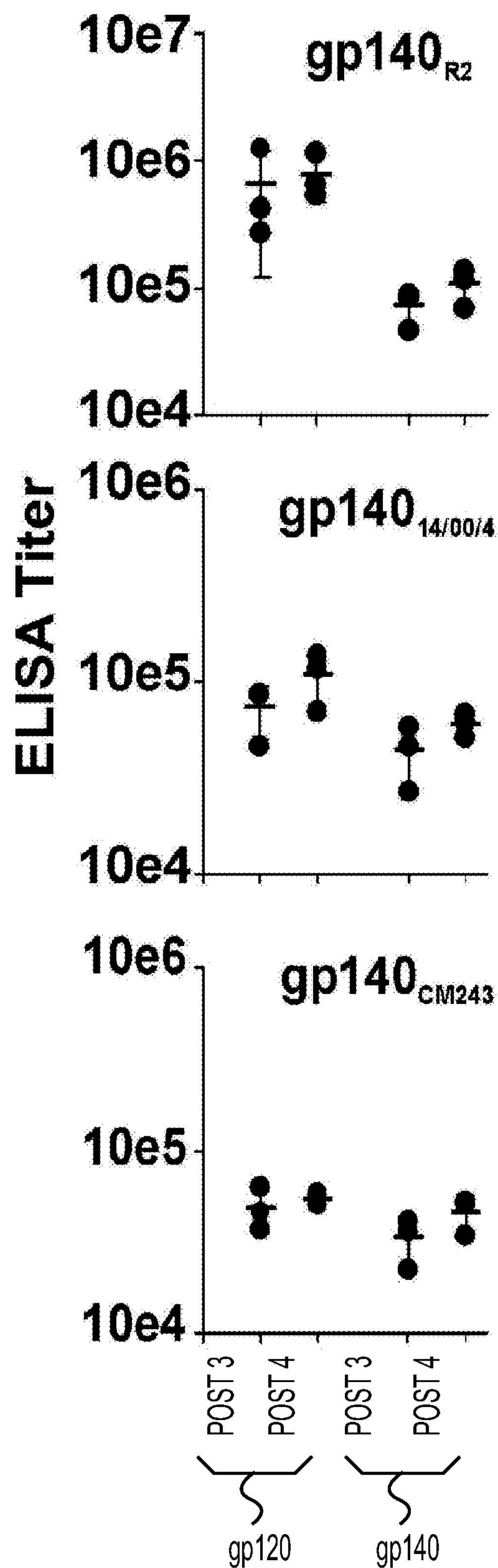
FIG. 2 shows IgG in sera of rabbits after four immunizations with either R2 strain gp120 or gp140, as measured by ELISA, using as antigens gp140 of the strains R2, 14/00/4, and CM243. The geometric mean IgG titers measured in sera or rabbits immunized with gp120 was about 10-fold higher against R2gp120 than against either of the other gp120s or R2gp140; these differences were all statistically significant by Student t test ($p<0.05$). IgG induced by gp140 bound similarly to each of the gp140s, and binding of IgG induced by gp120 and gp140 to 14/00/4 and CM243 gp140s was similar; these results did not differ significantly.
Figure 3:
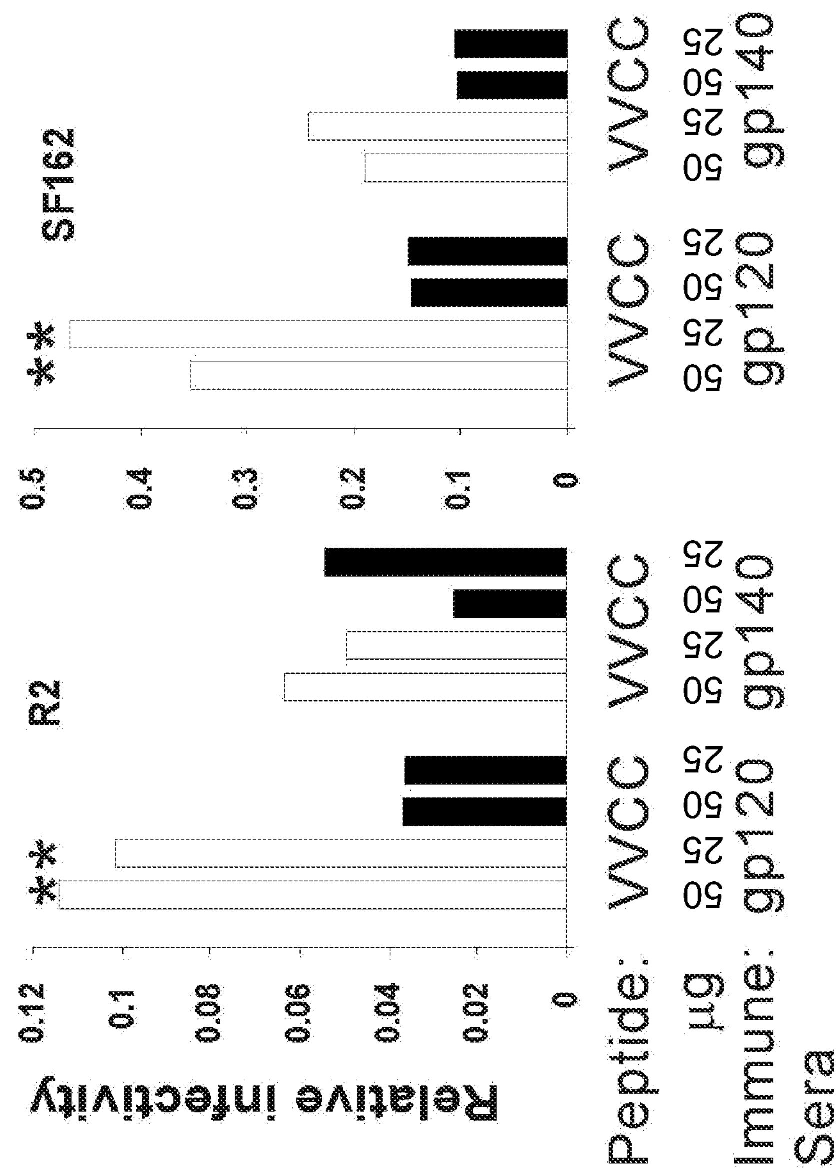
FIG. 3 shows blocking of neutralization of the HIV-1 strains R2 and SF162 by sera from rabbits immunized with R2gp120 or R2gp140 by synthetic, cyclized peptide with the amino acid sequence homologous to the V3 region of R2 Env (V), but not by control peptide (C). The sera were preincubated with the peptides at 50 or 25 μg/ml, then tested for neutralization of viruses. Results shown are averages of relative infectivity after incubation with sera in the presence of V or C peptides. Statistically significant inhibition of neutralization by the V peptide was observed for the sera from the 120- but not gp140-immunized rabbits (Student t test, $p<0.05$)
Figure 4:
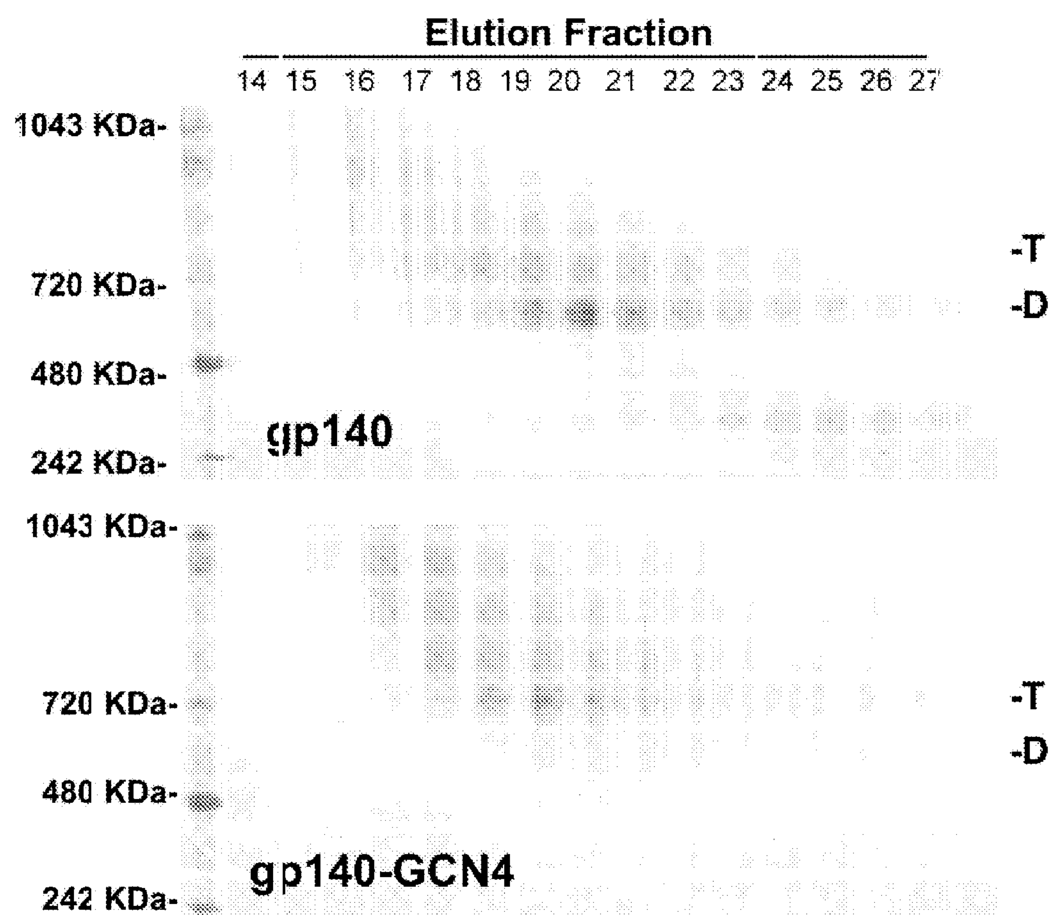
FIG. 4 shows Blue native gel electrophoresis of R2gp140 and R2gp140-GCN4. The approximate apparent molecular radii of trimer (T), dimer (D) and monomer in these analyses are 750, 500, and 250 KDa.

Research into the HIV-1 virus has been directed primarily at finding a mechanism to combat the virus. One of the more effective means is through immunization. The HIV-1 virus though readily mutates, and any antibodies produced are often effectively useless. Some antibodies, however, are capable of acting on many strains of the virus. One such source of these cross reactive antibodies is the R2 version of the Env glycoprotein.

Molecular analysis of the gp160 glycoprotein from the R2 Env has revealed the amino acid sequence of the protein and the nucleic acid sequence that encodes for it. Mutating the arginine residues at positions 517 and 520 to serine residues eliminates the site for endogenous cleavage into the gp120 and gp41 subunits. Further, truncating the nucleotide sequence at the transmembrane domain results in a non-membrane bound, non-cleaved version of gp160. This modified form of the gp160 from the R2 Env is referred to as R2gp140.

The recombinant R2gp140 produced using vaccinia virus for the immunization studies in rabbits associated approximately 40% as a trimeric compound, with the majority of the gp140 associating as a dimeric compound (Dong et al. (2003) J. Virol. 77:3119-3130). An increase in the association of the R2gp140 as a trimer would allow for a more concentrated production of the cross-reactive neutralizing antibodies. A highly purified R2gp140 oligomer is of use to allow for the absence of competition from more immunodominant epitopes exposed on the dimer, thereby permitting conversion of the cross-reactive response into a highly potent, rapid antibody response.

The present invention provides a fusion polypeptide that associates as an oligomer in high concentrations. The present invention provides fusion of the R2gp140 to a trimerization domain. The present invention provides a highly concentrated oligomer of non-membrane bound R2gp140 fused to a trimerization domain. The present invention provides high trimer concentrations of non-membrane bound R2gp140 fused to a trimerization domain. The present invention provides a fusion polypeptide that closely resembles the membrane bound Env protein. The present invention provides an immunogenic composition that can selectively induce cross-reactive neutralizing antibodies with high potency. The present invention further provides an immunogenic composition that induces antibodies that bind conformationally intact Env. The present invention also provides method of treating and/or preventing infection by HIV-1. The present invention provides methods to induce highly potent rapid cross-reactive antibodies as an immune response. Examples of methodology that may be used include, but are not limited to, the assays described herein in the Examples.

As used herein, the term "antibody" means an immunoglobulin molecule or a fragment of an immunoglobulin molecule having the ability to specifically bind to a particular antigen. Antibodies are well known to those of ordinary skill in the science of immunology. As used herein, the term "antibody" means not only full-length antibody molecules but also fragments of antibody molecules retaining antigen binding ability. Such fragments are also well known in the art and are regularly employed both in vitro and in vivo. In particular, as used herein, the term "antibody" means not only full-length immunoglobulin molecules but also antigen binding active fragments such as the well-known active fragments $F(ab')_2$, Fab, Fv, and Fd.

As used herein with respect to proteins and polypeptides, the term "recombinant" may include proteins and/or polypeptides and/or peptides that are produced or derived by genetic engineering, for example by translation in a cell of non-native nucleic acid or that are assembled by artificial means or mechanisms.

As used herein with respect to polypeptides and proteins, the term "isolated" may include a polypeptide or nucleic acid that, by the hand of man, exists apart from its native environment and is therefore not a product of nature. For example, an isolated polypeptide may exist in a purified form or may exist in a non-native environment such as, for example, a recombinant host cell.

As used herein, the term "analog" may include any polypeptide having an amino acid sequence substantially identical to a polypeptide, or peptide, of the invention, in which one or more residues have been conservatively substituted with a functionally similar residue, and further which displays substantially identical functional aspects of the polypeptides as described herein. Examples of conservative substitutions include substitution of one non-polar (hydrophobic) residue for another (e.g. isoleucine, valine, leucine or methionine) for another, substitution of one polar (hydrophilic) residue for another (e.g. between arginine and lysine, between glutamine and asparagine, between glycine and serine), substitution of one basic residue for another (e.g. lysine, arginine or histidine), or substitution of one acidic residue for another (e.g. aspartic acid or glutamic acid).

As used herein, a "homolog" may include any polypeptide having a tertiary structure substantially identical to a polypeptide of the invention which also displays the functional properties of the polypeptides as described herein.

As used herein, "trimerization domain" refers to a structural motif that aids the polymerization of expressed proteins. Trimerization domains may aid proteins to configure as though they were bound to the membrane. Trimerization domains, for example, may use coiled-coil motifs to polymerize. An example of a trimerization domain is seen in the basic leucine zipper. Basic leucine zippers typically correlate to a coiled coil of α-helices, whereby the positioning of leucine, or other hydrophobic amino acids, in the helices interact to form a hydrophobic core. An example of a basic leucine zipper is GCN4.

As used herein, "pharmaceutically acceptable carrier" may include any material which, when combined with an active ingredient, allows the ingredient to retain biological activity and is non-reactive with the subject's immune system. Examples may include, but are not limited to, standard pharmaceutical carriers such as a phosphate buffered saline (PBS) solution, water, emulsions, and various types of wetting agents.

As used herein, "fusion" may refer to nucleic acids and polypeptides that comprise sequences that are not found naturally associated with each other in the order or context in which they are placed according to the present invention. A fusion nucleic acid or polypeptide does not necessarily comprise the natural sequence of the nucleic acid or polypeptide in its entirety. Fusion proteins have the two or more segments joined together through normal peptide bonds. Fusion nucleic acids have the two or more segments joined together through normal phosphodiester bonds.

As used herein, "subject" may include the recipient of the treatment to be practiced according to the invention. The subject can be any animal, including a vertebrate. The subject will in most cases, preferably be a human, but may also be a domestic livestock, laboratory subject or pet animal.

As used herein, "cleavage" may refer to the severing of an amino acid or nucleotide sequence. By way of example, cleavage may occur with the use of enzymes, such as trypsin and chymotrypsin. By way of further example, nucleotide sequences can be cleaved with the use of restriction endonucleases.

The present invention provides a fusion polypeptide comprising the gp140 derived from the R2 Env of HIV-1 (R2gp140) and a trimerization domain. As used herein, a gp140 is a modified gp160, wherein the endogenous cleavage site is mutated and the amino acid sequence is truncated to remove all or part of the transmembrane domain.

Fusion Polypeptides of R2gp140 and a Trimerization Domain

The present invention provides a fusion polypeptide comprising fusion of non-cleaved, non-membrane bound, carboxyl terminal truncated gp160 derived from the R2 Env of HIV-1 (namely R2gp140) to a trimerization domain (namely R2gp140-trimerization domain fusion polypeptide). In some embodiments the trimerization domain is fused to the carboxyl terminus of R2gp140. In other embodiments, the trimerization domain is fused to the amino terminus In one embodiment, the amino acid sequence of R2gp140 may further encompass amino acid insertions, substitutions and/or deletions that have minimal to no effect on the activity, function or shape of the polypeptide. Examples of such substitutions include the substitution of one non-polar residue for another, the substitution of one polar residue for another, the substitution of one basic residue for another, or the substitution of one acidic residue for another. The R2gp140 may further include insertions, substitutions and/or deletions of amino acids in a comparison to the amino acid sequence of the native R2gp140 that yield minimal effect on the activity, function and/or structure of the polypeptide. Those skilled in the art will recognize non-natural amino acids may also be used. Non-natural amino acids include, for example, beta-alanine (beta-Ala), or other omega-amino acids, such as 3-amino propionic, 2,3-diamino propionic (2,3-diaP), 4-amino butyric and so forth, alpha-aminisobutyric acid (Aib), sarcosine (Sat), ornithine (Orn), citrulline (Cit), t-butylalanine (t-BuA), t-butylglycine (t-BuG), N-methylisoleucine (N-MeIle), phenylglycine (Phg), and cyclohexylalanine (Cha), norleucine (Nle), cysteic acid (Cya) 2-naphthylalanine (2-Nal); 1,2,3,4-tetrahydroisoquinoline-3-carboxylic acid (Tic); beta-2-thienylalanine (Thi); and methionine sulfoxide (MSO).

In other embodiments, a spacer amino acid or spacer amino acid sequences may separate the trimerization domain and the R2gp140. A spacer amino acid is an amino acid that separates the fused polypeptides of the present invention. Spacer amino acid sequences are a series of spacer amino acids. Spacer amino acid sequences may be as lengthy as 100 amino acid residues. Spacer amino acids may result as a by-product of molecular cloning techniques, for example, from PCR site directed mutagenesis and/or to avoid frame shifts and/or to use particular restriction endonucleases. Spacer amino acids may also be introduced to allow for optimization of the tertiary structure of the fused polypeptide.

In some embodiments, the trimerization domain is a coiled coil motif. In preferred embodiments, the trimerization domain is a basic leucine zipper motif, more preferably the GCN4 motif. Other coiled coil motifs may be used and are known in the art. By way of example, the bacteriophage T4 fibritin motif. Those skilled in the art will recognize that other known coiled-coil motifs may be used. Those skilled in the art will also recognize that coiled coils may be synthesized de novo, such as through strategic hydrophobic amino acid residue placement in heptad repeats.

In some embodiments, the present invention provides a fusion polypeptide comprising the R2gp140-trimerization domain fusion polypeptide fused to additional polypeptides. In some embodiments, there are one, two, three, four, or more additional polypeptides fused to the R2gp140-trimerization domain fusion protein. In some embodiments, the additional polypeptides are fused toward the amino terminus of the R2gp140-trimerization domain fusion polypeptide. In other embodiments, the additional polypeptides are fused toward the carboxyl terminus of the R2gp140-trimerization domain fusion polypeptide. In further embodiments, the additional polypeptides flank the R2gp140-trimerization domain fusion polypeptide.

In some embodiments, the additional polypeptides may comprise one or more epitopes, such as epitopes that stimulate T helper cell responses. T helper epitopes are epitopes that are capable of being recognized by T helper cells. In other embodiments, the additional polypeptides may comprise an affinity tag. By way of example, fusion of a polypeptide comprising an epitope and/or an affinity tag to the R2gp140-trimerization domain fusion polypeptide may aid purification and/or identification of the protein. By way of example, the additional polypeptide may be a His-tag, a myc-tag, an S-peptide tag, a MBP tag (maltose binding protein), a GST tag (glutathione S-transferase), a FLAG tag, a thioredoxin tag, a GFP tag (green fluorescent protein), a BCCP (biotin carboxyl carrier protein), a calmodulin tag, a Strep tag, an HSV-epitope tag, a V5-epitope tag, and a CBP tag. The use of such epitopes and affinity tags is known to those skilled in the art.

In further embodiments, the additional polypeptides may provide sites for cleavage of the protein. As an example, a polypeptide may be cleaved by hydrolysis of the peptide bond. In some embodiments, the cleavage is performed by a protease enzyme. In some embodiments cleavage occurs in a cell. In other embodiments, cleavage occurs through artificial manipulation and/or artificial introduction of a cleaving enzyme. By way of example, protease enzymes may include aspartic proteases, serine proteases, metalloproteases and cysteine proteases.

The polypeptides of the present invention may be prepared by any known techniques. For example, the polypeptides may be expressed through genetic engineering. By way of example, the translation of recombinant DNA. The polypeptides may also be prepared synthetically. By way of example, the polypeptide may be synthesized using the solid-phase synthetic technique initially described by Merrifield (J. Am. Chem. Soc. 85:2149-2154.), which is incorporated herein by reference. Other polypeptide synthesis techniques may be found, for example, Kent et al. (1985) Synthetic Peptides in Biology and Medicine, eds. Alitalo, Partanen, and Vakeri, Elsevier Science Publishers, pp. 295-358.

The fusion polypeptides of the present invention may be isolated or obtained in substantially pure form. Substantially pure means that the proteins and/or polypeptides and/or peptides are essentially free of other substances with which they may be found in nature or in vivo systems to an extent practical and appropriate for their intended use. In particular, the fusion proteins are sufficiently pure and are sufficiently free from other biological constituents of their host cells so as to be useful in, for example, generating antibodies, sequencing, or producing pharmaceutical preparations. By techniques well known in the art, substantially pure polypeptides may be produced in light of the nucleic acid and amino acid sequences disclosed herein. Because a substantially purified polypeptide of the invention may be admixed with a pharmaceutically acceptable carrier in a pharmaceutical preparation, the polypeptide may comprise only a certain percentage by weight of the preparation. The polypeptide is nonetheless substantially pure in that it has been substantially separated from the substances with which it may be associated in living systems.

Proteins and peptides of the invention may be prepared by any available means, including recombinant expression of the desired protein or peptide in eukaryotic or prokaryotic host cells (see U.S. Pat. No. 5,696,238). Methods for producing proteins or polypeptides of the invention for purification may employ conventional molecular biology, microbiology, and recombinant DNA techniques within the ordinary skill level of the art. Such techniques are explained fully in the literature. See, for example, Maniatis et al., (1989) Molecular Cloning: A Laboratory Manual, 2d ed. Cold Spring Harbor Laboratory Press; Glover, (1985) DNA Cloning: A Practical Approach, Vols. 1-4, IRL Press; Gait, (1984) Oligonucleotide Synthesis: A Practical Approach, IRL Press; Hames & Higgins, (1985) Nucleic Acid Hybridisation: A Practical Approach, IRL Press; Freshney, (1992) Animal Cell Culture: A Practical Approach, IRL Press; Perbal, (1984) A Practical Guide To Molecular Cloning, Wiley.

Oligomers of the gp140-trimerization Fused Polypeptide

The present invention provides for oligomers comprising the R2gp140-trimerization domain fusion polypeptide. Oligomers are protein complexes made up of two or more subunits. Oligomers are comprised of subunits that associate through protein-protein interactions. Each subunit of an oligomer is an independently produced polypeptide. Oligomers may be comprised of subunits wherein each subunit is the same polypeptide. Oligomers may be comprised of subunits wherein each subunit is a different polypeptide. Oligomers may be comprised of subunits wherein some subunits, but not all, are the same polypeptide.

In one embodiment of the present invention, the oligomer is comprised by multiple subunits wherein each subunit is the R2gp140-trimerization domain fusion polypeptide. In preferred embodiments, the oligomer is a trimer of subunits wherein each subunit is the R2gp140-trimerization domain fusion polypeptide. In other embodiments, the oligomer is a trimer of subunits wherein at least one subunit is the R2gp140-trimerization domain fusion polypeptide. Those skilled in the art will recognize that other gp140 variants fused to a trimerization domain may associate as an oligomer with the R2gp140-trimerization domain fusion polypeptide.

Nucleic Acids Encoding the R2gp140-trimerization Domain Fusion Polypeptide

The present invention also provides a nucleic acid encoding an amino acid sequence of the R2gp140-trimerization domain fusion polypeptide. Nucleic acid may include single or double stranded forms of deoxyribonucleotides or ribonucleotides or polymers thereof. It may further encompass known analogs of natural nucleotides that have comparable binding properties and are metabolized in a similar manner to naturally occurring nucleotides. Those skilled in the art will recognize that substitutions can be made in the nucleotide sequence without altering the resulting amino acids. Nucleic acid refers only to the primary and secondary structure of the molecule and is not limited to any particular tertiary form. In discussing the structure of particular double-stranded DNA molecules, sequences may be described herein according to the normal convention of giving only the sequence in the 5' to 3' direction along the nontranscribed strand of DNA (e.g., the strand having a sequence homologous to the mRNA). Transcriptional and translational control sequences are nucleic acid regulatory sequences, such as promoters, enhancers, polyadenylation signals, terminators, and the like, that provide for the expression of a coding sequence in a host cell.

A nucleic acid "coding sequence" is a double-stranded nucleic acid sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A polyadenylation signal and transcription termination sequence will usually be located 3' to the coding sequence. A nucleic acid may thereby "encode" the corresponding amino acid sequence.

The present invention also provides for intermediary nucleotide sequences to fuse the nucleic acid encoding the R2gp140 to the nucleic acid encoding the trimerization domain. Those skilled in the art will recognize intermediary nucleotides may be necessary to ensure proper codon translation. Those skilled in the art will further recognize that intermediary nucleotides may code for a spacer amino acid or spacer amino acid sequences.

The present invention also provides a vector comprising a nucleic acid encoding the R2gp140-trimerization domain fusion polypeptide. A vector may be any of a number of nucleic acids into which a desired sequence may be inserted by restriction and ligation for transport between different genetic environments or for expression in a host cell. Vectors are typically composed of DNA, although RNA vectors are also available. Vectors include, but are not limited to, plasmids and phagemids. A cloning vector is one which is able to replicate in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium or just a single time per host before the host reproduces by mitosis. In the case of phage, replication may occur actively during a lytic phase or passively during a lysogenic phase.

Vectors may further contain a promoter sequence. A promoter may include an untranslated nucleic acid sequence usually located upstream of the coding region that contains the site for initiating transcription of the nucleic acid. The promoter region may also include other elements that act as regulators of gene expression. In further embodiments of the invention, the expression vector contains an additional region to aid in selection of cells that have the expression vector incorporated. The promoter sequence is often bounded (inclusively) at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains responsible for the binding of RNA polymerase. Eukaryotic promoters will often, but not always, contain "TATA" boxes and "CAT" boxes. Commonly used promoters are derived from polyoma, bovine papilloma virus, CMV (cytomegalovirus, either murine or human), Rouse sarcoma virus, adenovirus, and simian virus 40 (SV40). Other control sequences (e.g., terminator, polyA, enhancer, or amplification sequences) can also be used.

Vectors may further contain one or more marker sequences suitable for use in the identification and selection of cells which have been transformed or transfected with the vector. Markers include, for example, genes encoding proteins which increase or decrease either resistance or sensitivity to antibiotics or other compounds, genes which encode enzymes whose activities are detectable by standard assays known in the art (e.g., □-galactosidase or alkaline phosphatase), and genes which visibly affect the phenotype of transformed or transfected cells, hosts, colonies or plaques. Preferred vectors are those capable of autonomous replication and expression of the structural gene products present in the DNA segments to which they are operably joined.

An expression vector is one into which a desired nucleic acid sequence may be inserted by restriction and ligation such that it is operably joined to regulatory sequences and may be expressed as an RNA transcript. Expression refers to the transcription and/or translation of an endogenous gene, transgene or coding region in a cell. An expression vector is constructed so that the polypeptide coding sequence is located in the vector with the appropriate regulatory sequences, the positioning and orientation of the coding sequence with respect to the control sequences being such that the coding sequence is transcribed and translated under the "control" of the control sequences (i.e., RNA polymerase which binds to the DNA molecule at the control sequences transcribes the coding sequence). The control sequences may be ligated to the coding sequence prior to insertion into a vector, such as the cloning vectors described above. Alternatively, the coding sequence can be cloned directly into an expression vector which already contains the control sequences and an appropriate restriction site. If the selected host cell is a mammalian cell, the control sequences can be heterologous or homologous to the coding sequence, and the coding sequence can either be genomic DNA containing introns or cDNA.

A "heterologous" region of a DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

As used herein, DNA sequences are "substantially homologous" when at least about 85% (preferably at least about 90% and most preferably at least about 95%) of the nucleotides match over the defined length of the DNA sequences. Sequences that are substantially homologous can be identified in a Southern hybridization experiment under, for example, stringent conditions as defined for that particular system. Defining appropriate hybridization conditions is within the skill of the art.

A coding sequence and regulatory sequences are operably joined when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide.

The present invention also provides a nucleic acid comprised by the nucleic acid encoding the R2gp140-trimerization domain fusion polypeptide and another nucleic acid encoding additional polypeptides. The additional polypeptides may be sites of cleavage and/or affinity or epitope tags, or other epitopes. Those skilled in the art will recognize the need to avoid frame shifts of the codon reading frame to properly express the fused polypeptide. Those skilled in the art will recognize a frame shift may be avoided with the addition of extra nucleotides, such as by polymerase chain reaction (PCR). Those skilled in the art will recognize that nucleotides encoding spacer amino acids may be required to avoid a frame shift.

In some embodiments, the nucleic acid encoding the additional polypeptides is located upstream of the 5' end of the nucleic acid encoding the R2gp140-trimerization domain fusion polypeptide. In other embodiments the nucleic acid encoding the additional polypeptides is located downstream of the 3' end of the nucleic acid encoding the R2gp140-trimerization domain fusion polypeptide. In further embodiments, nucleic acid encoding additional polypeptides flanks the nucleic acid encoding the R2gp140-trimerization domain fusion polypeptide. In further embodiments, nucleic acid encoding additional polypeptides is placed between the nucleic acid encoding the R2gp140 and the nucleic acid encoding the trimerization domain.

The present invention also provides the transformation and/or transfection of nucleic acid encoding the R2gp140-trimerization domain fusion polypeptide. Transformation is the introduction of exogenous or heterologous nucleic acid to the interior of a prokaryotic cell. Transfection is the introduction of exogenous or heterologous nucleic acid to the interior of a eukaryotic cell. The transforming or transfecting nucleic acid may or may not be integrated (covalently linked) into chromosomal DNA making up the genome of the cell. In prokaryotes, for example, the transforming nucleic acid may be maintained on an episomal element such as a plasmid or viral vector. With respect to eukaryotic cells, a stably transfected cell is one in which the transfecting nucleic acid has become integrated into a chromosome so that it is inherited by daughter cells through chromosome replication. This stability is demonstrated by the ability of the eukaryotic cell to establish cell lines or clones comprised of a population of daughter cells containing the transfected nucleic acid.

Higher eukaryotic cell cultures may be used to express the proteins of the present invention, whether from vertebrate or invertebrate cells, including insects, and the procedures of propagation thereof are known. See, for example, Kruse and Patterson (1973) Tissue Culture, Academic Press.

Suitable host cells for expressing the polypeptides of the present invention in higher eukaryotes include: 293 (human embryonic kidney) (ATCC CRL-1573); 293F (Invitrogen, Carlsbad Calif.); 293T and derivative 293T/17 (293tsA1609neo and derivative ATCC CRL-11268) (human embryonic kidney transformed by SV40 T antigen); COS-7 (monkey kidney CVI line transformed by SV40)(ATCC CRL1651); BHK (baby hamster kidney cells) (ATCC CRL10); CHO (Chinese hamster ovary cells); mouse Sertoli cells; CVI (monkey kidney cells) (ATCC CCL70); VERO76 (African green monkey kidney cells) (ATCC CRL1587); HeLa (human cervical carcinoma cells) (ATCC CCL2); MDCK (canine kidney cells) (ATCC CCL34); BRL3A (buffalo rat liver cells) (ATCC CRL1442); W138 (human lung cells) (ATCC CCL75); HepG2 (human liver cells) (HB8065); and MMT 060652 (mouse mammary tumor) (ATCC CCL51).

It will be appreciated that when expressed in mammalian tissue, the recombinant fusion polypeptide products may have higher molecular weights than expected due to post-translational modifications, such as glycosylation. It is therefore intended that partially or completely glycosylated forms of fusion polypeptides of the present invention having molecular weights somewhat different are within the scope of this invention.

Fusion Gene/Protein Construction & Polypeptide Linkers

The term "fusion protein" herein refers to the protein resulting from the expression of gp120 and gp41 operatively-linked coding sequences. These fusion proteins include constructs in which the C-terminal portion of gp120 is fused to the N-terminal portion of gp41 via an intervening in frame linker sequence.

Linkers are generally polypeptides of between 6 and 28 amino acids in length. The linkers joining the two molecules are preferably designed to allow the two molecules to fold and act independently of each other, not have a propensity for developing an ordered secondary structure which could interfere with the functional subunits of the two proteins, have minimal hydrophobic or charged characteristic which could interact with the functional protein subunits and prevent complete dissociation of gap 120 from gp41 but still allow limited conformational changes that can lead to exposure of conserved epitopes able to elicit broadly cross-reactive HIV neutralizing antibodies.

Typically surface amino acids in flexible protein regions include Gly, Asn and Ser. Virtually any permutation of amino acid sequences containing Gly, Asn and Ser would be expected to satisfy the above criteria for a linker sequence. Other neutral amino acids, such as Thr and Ala, may also be used in the linker sequence. Preferably such neutral amino acids will have a relatively small surface area (160 A2, or less). Additional amino acids may also be included in the linkers due to the addition of unique restriction sites to facilitate construction of the fusions.

Exemplary linkers of the present invention include sequences selected from the group of formulas: $(GlySer)_n$, $(Gly_3Ser)_n$, $(Gly_4Ser)_n$, $(Gly_5Ser)_n$, $(Gly_nSer)_n$ or $(AlaGlySer)_n$ where n can take a value a range 3 to 12. Additional examples of preferred linkers are set out in SEQ ID NO: 9 through 13.

The present invention is however, not limited by the form, size, composition or number of linker sequences employed. The only requirement of the linker is that, functionally, it does not interfere adversely with the folding and function of the individual molecules of the fusion, and otherwise allows for expression of the chimeric fusion molecule. One test of linker functionality is through inhibition of syncytia formation and reporter gene (β-gal and luciferase) assays. Linker constructs of this invention form fusion proteins displaying at least 50% inhibition (at about 100 ng/ml fusion protein) by either assay. The fusion proteins also specifically bind antibodies raised against gp120 and gp41.

The present invention also includes linkers in which an endopeptidase recognition sequence is included. Such a cleavage site may be valuable to separate the individual components of the fusion to, for example, determine if they are properly folded and active in vitro. Examples of various endopeptidases include, but are not limited to, Plasmin, Enterokinase, Kallikrein, Urokinase, Tissue Plasminogen activator, clostripain, Chymosin, Collagenase, Russell's Viper Venom Protease, Postproline cleavage enzyme, V8 protease, Thrombin and Factor Xa.

Immunogenic Compositions

The present invention also provides immunogenic compositions comprising the R2gp140-trimerization domain fusion polypeptide. Immunogenic compositions are compositions that are capable of generating an immune response. Immune responses may be directed to certain immunodominant regions of the composition. In some embodiments, association of the R2gp140-trimerization domain fusion polypeptide presents a novel epitope or novel epitopes for antibody binding. In one embodiment of the present invention, the immunodominant V3 region of the R2gp140 is masked.

The present invention provides for administration of an immunogenic composition comprised of the R2gp140-trimerization domain fusion polypeptide to a subject. In preferred embodiments, the immunogenic composition is comprised of an oligomer wherein the oligomer is comprised by the R2gp140-trimerization domain fusion polypeptide. In more preferred embodiments, the oligomer is a trimer of the R2gp140-trimerization fusion polypeptide.

In some embodiments of the present invention, the immunogenic composition provides a highly potent and rapid antibody response. In preferred embodiments, the immunogenic compositions of the present invention provide cross-reactive neutralizing antibodies.

The fusion polypeptide of the immunogenic composition can be administered as part of a composition. For example, in adjuvant. As used herein, "adjuvant" refers to an agent which, while not having any specific antigenic effect in itself, may stimulate the immune system, increasing the response to a vaccine. In some embodiments, the adjuvant comprises a Toll like receptor (TLR) 4 ligand, in combination with a saponin. The Toll like receptor (TLR) 4 ligand may be for example, an agonist such as a lipid A derivative particularly monophosphoryl lipid A or more particularly 3 Deacylated monophoshoryl lipid A (3 D-MPL). 3 D-MPL is sold under the trademark MPL® by Corixa Corporation and primarily promotes CD4+ T cell responses with an IFN-g (Th1) phenotype.

It can be produced according to the methods disclosed in GB 2220211A. Chemically, it is a mixture of 3-deacylated monophosphoryl lipid A with 3, 4, 5 or 6 acylated chains. In one embodiment in the compositions of the present invention small particle 3 D-MPL is used. Small particle 3 D-MPL has a particle size such that it may be sterile-filtered through a 0.22 μm filter. Such preparations are described in WO 94/21292.

The adjuvant may also comprise one or more synthetic derivatives of lipid A which are known to be TLR 4 agonists including, but not limited to: OM174 (2-deoxy-6-o-[2-deoxy-2-[(R)-3-dodecanoyloxytetra-decanoylamino]-4-o-phosphono-β-D-glucopyranosyl]-2-[(R)-3-hydroxytetradecanoylamino]-α-D-glucopyranosyldihydrogenphosphate), as described in WO 95/14026; OM 294 DP (3S,9R)-3-[(R)-dodecanoyloxytetradecanoylamino]-4-oxo-5-aza-9(R)-[(R)-3-hydroxytetradecanoylamino]decan-1,10-diol,1,10-bis(dihydrogenophosphate), as described in WO 99/64301 and WO 00/0462; and, OM 197 MP-Ac DP (3S-, 9R)-3-[(R)-dodecanoyloxytetradecanoylamino]-4-oxo-5-aza-9-[(R)-3-hydroxytetradecanoylamino]decan-1,10-diol,1-dihydrogenophosphate 10-(6-aminohexanoate) (WO 01/46127).

Other TLR4 ligands which may be used include, but are not limited to, alkyl Glucosaminide phosphates (AGPs) such as those disclosed in WO 98/50399 or U.S. Pat. No. 6,303,347 (processes for preparation of AGPs are also disclosed), or pharmaceutically acceptable salts of AGPs as disclosed in U.S. Pat. No. 6,764,840. Some AGPs are TLR4 agonists, and some are TLR4 antagonists. Both can be used as one or more adjuvants in the compositions of the invention.

A preferred saponin for use in the present invention is Quil A and its derivatives. Quil A is a saponin preparation isolated from the South American tree Quilaja Saponaria Molina and was first described as having adjuvant activity by Dalsgaard et al. (1974) Saponin adjuvants, Archiv. für die gesamte Virusforschung, Vol. 44, Springer Verlag, pp. 243-254. Purified fragments of Quil A have been isolated by HPLC which retain adjuvant activity without the toxicity associated with Quil A (EP 0 362 278), for example QS7 and QS21 (also known as QA7 and QA21). QS21 is a natural saponin derived from the bark of Quillaja saponaria Molina which induces CD8+ cytotoxic T cells (CTLs), Th1 cells and a predominant IgG2a antibody response and is a preferred saponin in the context of the present invention.

Particular formulations of QS21 have been described which are particularly preferred, these formulations further comprise a sterol (WO 96/33739). The saponins forming part of the present invention may be separate in the form of micelles, mixed micelles (preferentially, but not exclusively with bile salts) or may be in the form of ISCOM matrices (EP 0109942 B1), liposomes or related colloidal structures such as worm-like or ring-like multimeric complexes or lipidic/layered structures and lamellae when formulated with cholesterol and lipid, or in the form of an oil in water emulsion (for example as in WO 95/17210). The saponins may be associated with a metallic salt, such as aluminium hydroxide or aluminium phosphate (WO 98/15287). In some embodiments, the saponin is presented in the form of a liposome, ISCOM or an oil in water emulsion.

In some embodiments, adjuvants are combinations of 3D-MPL and QS21 (EP 0671948) and oil in water emulsions comprising 3D-MPL and QS21 (WO 95/17210, WO 98/56414).

The fusion polypeptide of the immunogenic composition is typically an isolated and purified protein. The protein is preferably purified to at least 95% purity, more preferably at least 98% purity, and still more preferably at least 99% purity. Methods of purification that retaining the conformation of the protein are known in the art. The purified protein is preferably present in a pharmaceutical composition with a pharmaceutically acceptable carrier, diluent, excipient or stabilizer present.

The formulation of immunogenic compositions of the invention will employ an effective amount of the protein or polypeptide antigen. That is, there will be included an amount of antigen which, in combination with the adjuvant, will cause the subject to produce a specific and sufficient immunological response so as to impart protection to the subject from subsequent exposure to an HIV virus. When used as an immunogenic composition, the formulation will contain an amount of antigen which, in combination with the adjuvant, will cause the subject to produce specific antibodies which may be used for diagnostic or therapeutic purposes.

The immunogenic compositions of the invention may be useful for the prevention or therapy of HIV-1 infection. While all animals that can be afflicted with HIV-1 can be treated in this manner, the invention, of course, is particularly directed to the preventive and therapeutic use of the vaccines of the invention in man.

The immunogenic compositions are administered in any conventional manner which will introduce the composition into the animal, usually by injection. For oral administration the immunogenic composition can be administered in a form similar to those used for the oral administration of other proteinaceous materials. The precise amounts and formulations for use in either prevention or therapy can vary depending on the circumstances of the inherent purity and activity of the antigen, any additional ingredients or carriers, the method of administration and the like.

By way of non-limiting illustration, the dosages administered will typically be, with respect to the R2gp140-trimerization domain antigen, a minimum of about 0.1 mg/dose, more typically a minimum of about 1 mg/dose, and often a minimum of about 10 mg/dose. The maximum dosages are typically not as critical. Usually, however, the dosage will be no more than 500 mg/dose, often no more than 250 mg/dose. These dosages can be suspended in any appropriate pharmaceutical vehicle or carrier in sufficient volume to carry the dosage. Generally, the final volume, including carriers, adjuvants, and the like, typically will be at least 0.1 ml, more typically at least about 0.2 ml. The upper limit is governed by the practicality of the amount to be administered, generally no more than about 0.5 ml to about 1.0 ml.

In an alternative format, immunogenic compositions may be prepared as vaccine vectors which express the fusion polypeptides of the invention in the host animal. Any available vaccine vector may be used, including live Venezuelan Equine Encephalitis virus (see U.S. Pat. No. 5,643,576), poliovirus (see U.S. Pat. No. 5,639,649), pox virus (see U.S. Pat. No. 5,770,211) and vaccina virus (see U.S. Pat. Nos. 4,603,112 and 5,762,938). Alternatively, naked nucleic acid encoding a protein or peptide of the invention may be administered directly to effect expression of the antigen (see U.S. Pat. No. 5,739,118).

Methods of Inducing a Cross-Reactive Immune Response to HIV-1

The present invention also provides methods of inducing cross-reactive immune response to HIV-1. In some embodiments, the methods of inducing a cross-reactive immune response comprising administering the fusion polypeptide of the present invention to a subject. In some embodiments, the methods of inducing a cross-reactive immune response comprising administering the immunogenic compositions of the present invention to a subject. In other embodiments, the methods of inducing a cross-reactive immune response comprising administering the nucleic acids encoding the fusion polypeptides of the present invention to a subject. In further embodiments, vectors comprised of nucleic acids encoding the fusion polypeptides of the present invention are administered. In other embodiments, naked nucleic acids encoding the fusion polypeptides of the present invention are administered. Routes of administration to a subject are known in the art. For example, they may include oral, rectal, nasal, topical, parenteral, subcutaneous, intramuscular, intravenous and/or intradermal routes.

An immune response can be manipulated to maximize the amount of antibodies produced and present in the sera of a subject. One such method is achieved by subjecting a subject to an initial immunogenic composition, referred to as priming, and later challenging the subject's immune response by repeating the exposure, referred as boosting. In one method of use, an oligomer comprised of the R2gp140-trimerization domain fusion polypeptide is used to prime a subject, and the same oligomer is used to boost the subject. In other methods, the boost is achieved with an oligomer comprised by other gp140-trimerization domain fusion polypeptides. In other methods, the boost is an oligomer comprised of the R2gp140-trimerization domain fusion polypeptide and other gp140-trimer domain fusion polypeptides. Dosage schedule of administration and efficacy of the immunogenic composition can be determined by methods known in the art. Extra dosages may be chosen to maintain and/or reinforce the immune response. The dosage regimen will also, at least in part, be determined by the need of the subject and be dependent on the judgment of the practitioner. In some embodiments, the methods induce cross-reactive antibodies to HIV-1 by presenting a novel antigen in a subject. In some embodiments, the methods provide for masking of epitopes that are immunodominant in native gp120. In other embodiments, the methods provide for antibody binding to epitopes that are taciturn in native gp120. In some embodiments, the methods induce neutralizing antibodies in the subject. In preferred embodiments, the neutralizing antibodies are cross-reactive, more preferably, they are also highly potent. In some embodiments, the methods induce antibodies that bind conformationally intact HIV-1 Env protein. In some embodiments, the methods induce a rapid antibody response in the subject.

The methods of inducing a cross-reactive immune response may be used to treat a subject. The methods may also be used as a prophylactic to induce antibody production in a subject. The methods may be used to prevent subsequent HIV-1 infection in a subject. The methods may be used protect a subject from exposure to HIV-1. The methods of inducing a cross-reactive response may facilitate vaccination of a subject to HIV-1.

Without further description, it is believed that one of ordinary skill in the art can, using the preceding description and the following illustrative examples, make and utilize the claimed invention. The following working examples therefore, specifically point out preferred embodiments of the present invention, and are not to be construed as limiting in any way the remainder of the disclosure. All articles, publications, patents and documents referred to throughout this application are hereby incorporated by reference in their entirety.

EXAMPLES

Example 1

Figure 5:
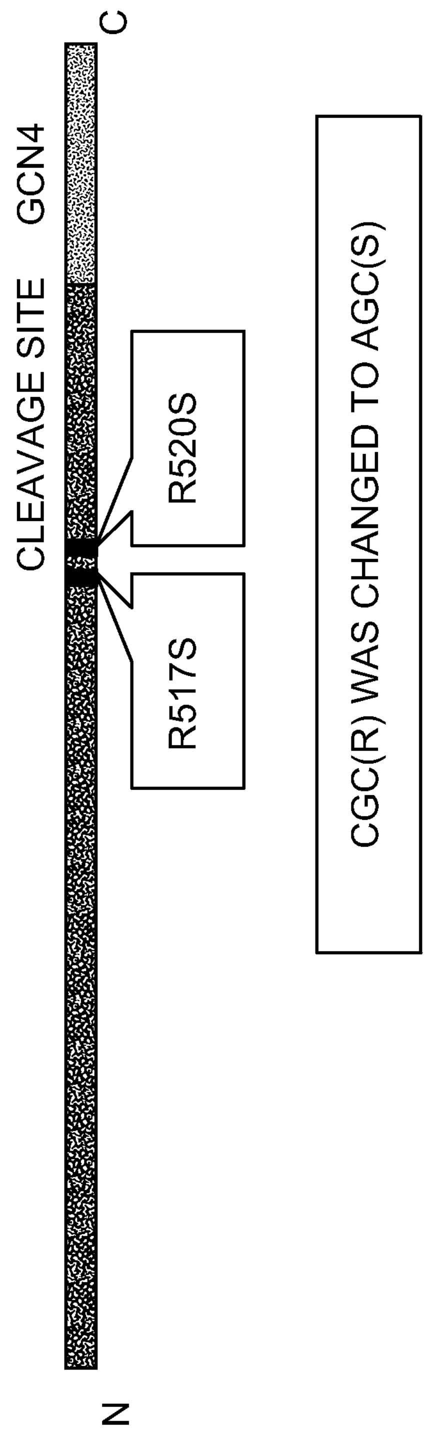
FIG. 5 shows a schematic of R2gp140-GCN4.

Materials and methods. The gene encoding R2gp140-GCN4 was constructed into a promoter modified mammalian expression vector pcDNA 3.1 Hygro(+) (Invitrogen). To increase transgene expression level, the enhanced CMV promoter from phCMV1 vector (Gelantis) was introduced into pcDNA 3.1 Hygro(+). The Hygromycin selection marker allows the selection of transfected 293T cells, which are resistant to the commonly used Geneticin (G418) antibiotic. Human codon optimized R2gp140, with mutated cleavage sites, was fused with a trimeric coil-coiled GCN4 motif at the C-terminal end (FIG. 5). This construction was done by generating a Hind III restriction site upstream to the stop codon of R2gp140 by QuikChange Mutagenesis (Strategene) using primers: forward 5'-CTGTGGTACATCAAG AAGCTTTAATAATCTAGAGGG (SEQ ID NO: 7) and reverse 5'-CCCTCTAGATTATTA AAGCTTCTTGATGTACCACAG (SEQ ID NO: 8) (the Hind III site is underlined). A GCN4 fragment flanked by Hind III sites was ligated to the Hind III digested R2gp140. The correct orientation of GCN4 was confirmed by both enzymatic digestion and DNA sequencing. The resulting R2gp140-GCN4 (SEQ ID NO: 3) was then cloned into the promoter modified pcDNA 3.1 Hygro(+). This plasmid was referred to as pLY-1. FIG. 5 depicts a schematic of the constructed R2gp140-GCN (SEQ ID NO: 4).

Plasmid pLY-1 was then used to transfect 293T and 293F cells. Stable cell lines were generated through Hygromycin selection and limiting dilution. The resulting 293T and 293F stable cell lines expressing R2gp140-GCN were then grown to increase the scale of protein expression and purification. The same plasmid construct without the GCN4 motif was also used to generate stable 293T and 293F cells for comparison.

Table 1 lists the cell lines generated and the approximate protein yield from each cell line grown in its respective medium. The stable 293T cell line expressing R2gp140-GCN4 was grown in 1700 $cm^2$ DMEM supplemented with 10% serum (D-10) for 4 days. The serum-containing medium was then replaced with OptiMEM and cells were grown for additional 4 days. The 293F, cells were first grown in 150 $cm^2$ flasks in D-10. Cells from two confluent flasks were then dislodged in 293 serum free media (293 SFM), seeded into 500 ml shaker flasks at a density of $1\times10^6$/ml, and allowed to grow in suspension while shaking at a rate of 125 rpm. Cells were diluted to 0.5 to $0.7\times10^6$/ml when the density was more than $1.5\times10^6$/ml on the next day. Trypan blue analysis was carried out everyday to monitor cell growth. Cells were allowed to grow for an additional 3 to 4 days until dead cells were observed.

TABLE 1

Cell lines generated and the approximate protein yield from each cell line

| Cell line | | Protein yield (mg) |
|---|---|---|
| | Culture medium OptiMEM (Invitrogen) | |
| 293T-R2gp140 | 1200 ml (10 × 1700 $cm^2$ roller bottles) | 28 mg |
| 293T-R2gp140-GCN | 1080 ml (9 × 1700 $cm^2$ roller bottles) | 25 mg |
| | Culture medium 293 SFM (Invitrogen) | |
| 293F-R2gp140 | 600 ml (3 × 500 ml shaker flasks) | 28 mg |
| 293F-R2gp140-GCN | 600 ml (3 × 500 ml shaker flasks) | 28 mg |

Culture supernatant from 293T or 293F cell cultures was collected, centrifuged, and filtered through a 0.22μ membrane. The cleared supernatant was applied to Lentile lectin affinity purification and eluted with 0.5 M methylmannopyranoside. The elution was concentrated and buffer exchanged with PBS. Purified protein was analyzed on SDS-PAGE using a 4-12% Bis-Tris Nupage gel (Invitrogen) in reducing conditions and a 3-12% Native PAGE gel from the Blue native (BN) gel system (Invitrogen).

Figures 6A, 6B, 6C, 6D:
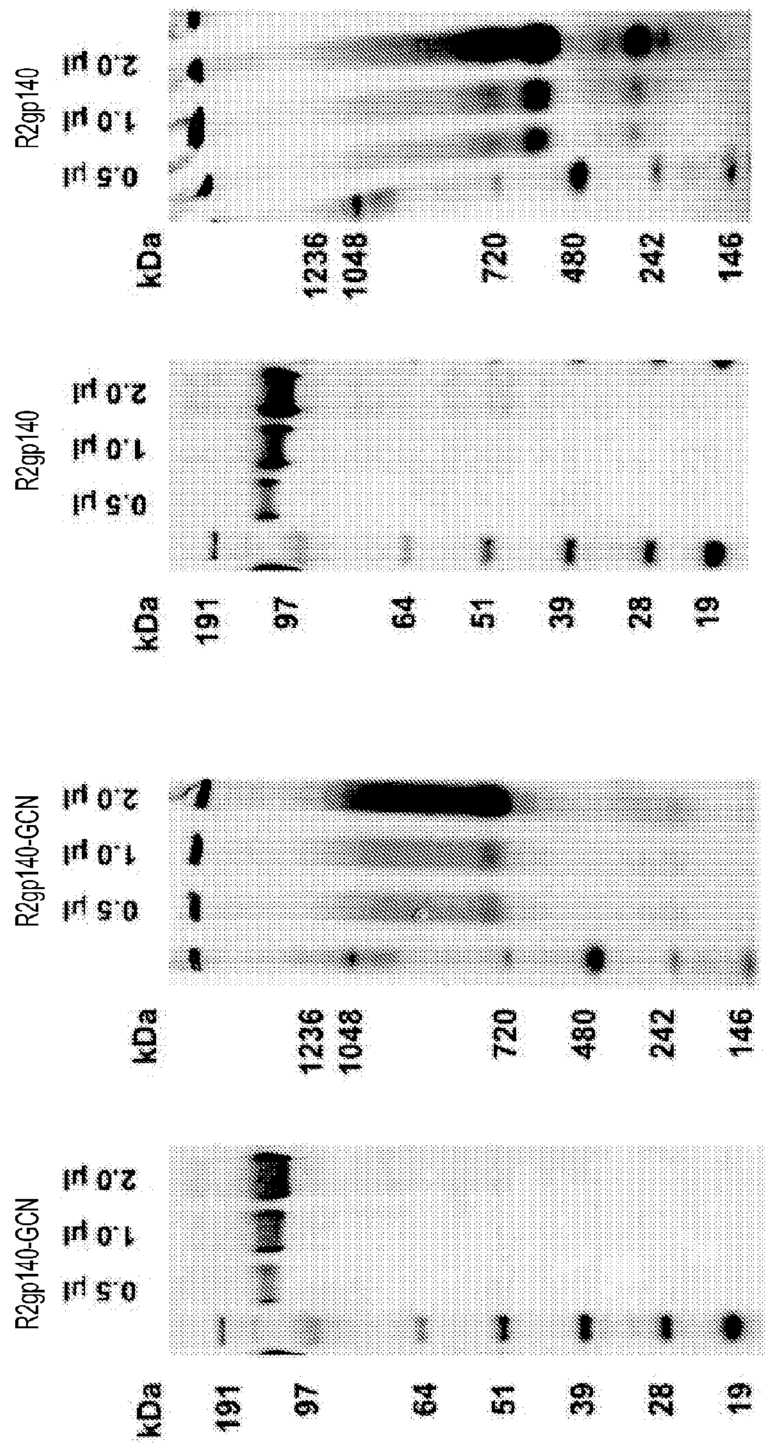
FIGS. 6A-6D show PAGE analysis of purified R2gp140 with and without GCN4 in native and denaturing conditions. 0.5, 1, 2 μl of purified R2gp140 with and without GCN4 was analyzed on SDS-PAGE using a 4-12% Bis-Tris Nupage gel (Invitrogen) in reducing condition (FIGS. 6A and 6C) and a 3-12% Native PAGE gel (Invitrogen) (FIGS. 6B and 6D).

Results. Denaturing conditions indicate the size and expression of the R2gp140-GCN4 protein was comparable to R2gp140 (FIGS. 6A and 6C). The use of non-denaturing conditions allowed for analysis of the effects on oligomer assembly the GCN4 motif causes. The presence of the GCN4 provided a prominent putative trimer band at ~750 kDa (FIG. 6B). The absence of the GCN4 motif presented two additional bands of putative dimer and monomer at ~500 kDa and ~250 kDa, respectively (FIG. 6D). These data indicate that the GCN4 motif increases the preference of R2gp140 to coalesce as a trimer.

Example 2

Materials and Methods. Purified R2gp140±GCN4 (produced as described in Example 1) was subjected to size exclusion chromatography using Superdex 200 (GE healthcare) column. Approximately 1.5 mg of protein was analyzed on a Superdex 200 10/300 column calibrated with molecular weight standards to observe oligomeric species and to estimate the approximate molecular mass of the different species. Fractions of 400 μl were collected. 10 μl and 1 μl of each fraction were analyzed using the BN gel system (Invitrogen) for coomassie blue and western blot detection (FIGS. 7 and 8) following manufacturer's instructions. For immunodetection in western blotting, polyclonal rabbit anti gp140 serum R2143 was used. The remaining protein was then applied to HiLoad 16/60 Superdex 200 prep grade gel filtration column.

Figure 7A:
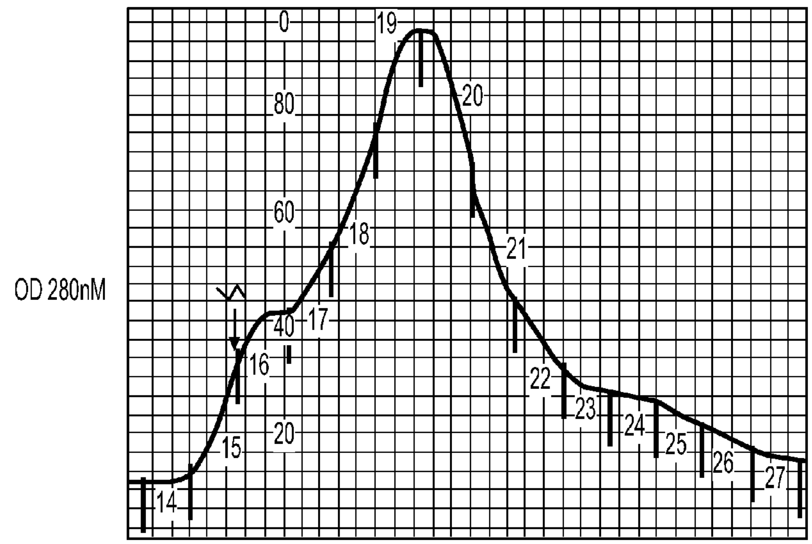
FIGS. 7A-7C show size exclusion chromatography analysis of R2gp140 without GCN4 purified from 293T. 1.5 mg of protein was run on a calibrated Superdex 200 10/300 Gel filtration column. 400 μl fractions were collected; the molecular weight was estimated from a calibrated curve (FIG. 7A). 1 μl of each fraction was analyzed by BN PAGE followed by western blotting. Rabbit anti gp140, R2143 antibody was used for immunodetection followed by HRP conjugated anti-rabbit antibody (FIG. 7B). 5 μl of each fraction was analyzed by BN PAGE stained with coomassie (FIG. 7C).
Figure 7B:
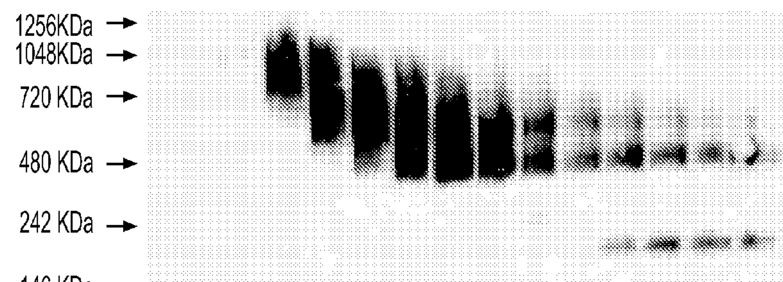
Figure 7C:
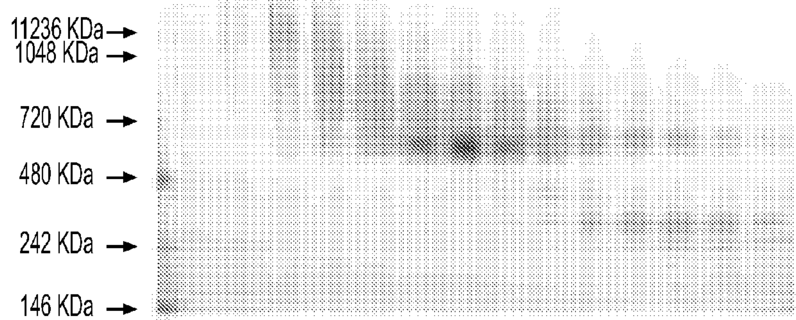

Results. The presence of the GCN4 motif shifted the elution profile to a much earlier peak after the void volume, as well as producing a sharper decline in detection of protein in later fractions (FIGS. 7A and 8A). These data suggest the GCN4 leads to a heavier overall protein complex, namely a trimer. Coomassie stain and western blot confirm the elution profiles, indicating the GCN4 produces predominantly one species of ~750 kDa, the putative trimer based on the combined masses (FIGS. 8B and 8C). Absence of the GCN4 motif produced putative dimer (~500 kDa) and monomer (~250 kDa) bands, in addition to the putative trimer (FIGS. 7B and 7C). The presence of the GCN4 significantly reduces the presence of the putative dimer and monomer, indicating the GCN4 creates a preference for the fusion protein to assemble as a trimer.

Example 3

Figure 9:
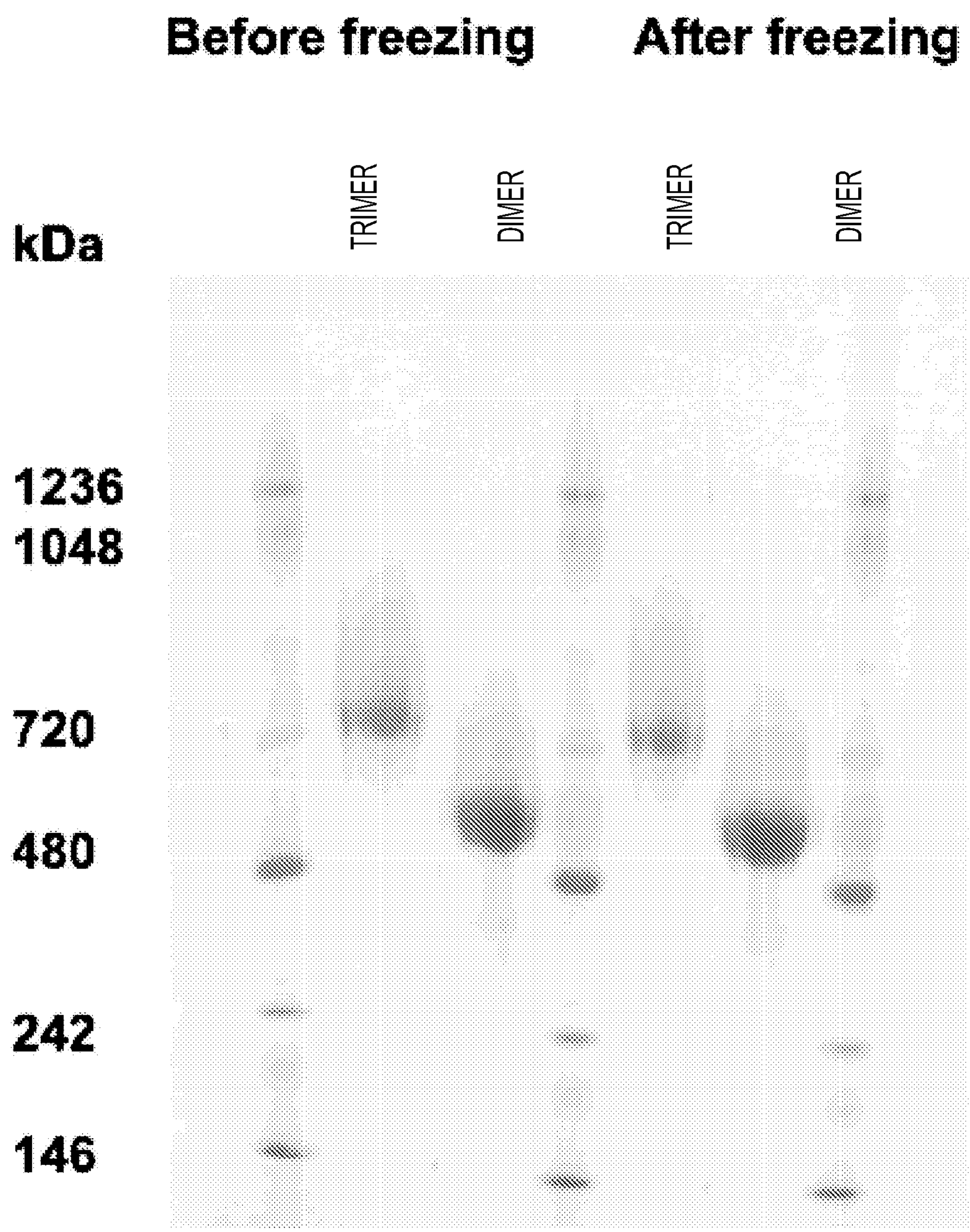
FIG. 9 shows native PAGE analysis of isolated dimmer and trimer R2gp140+ and −GCN4 from fractions collected from gel filtration. 20 μl of protein was frozen in −80° C. for four days and thawed to be analyzed. 10 μl of protein kept in 4° C. and freeze thawed were resolved on a 3-12% Native PAGE gel.

Materials and Methods. The putative trimer and dimer fractions (obtained from Example 2) were collected after gel filtration. A portion of the sample was stored at −80° C. for four days and then thawed. The thawed sampled was run on a BN-PAGE side by side with sample that had been stored at 4° C. for comparison (FIG. 9).

Results. Before and after freezing the fractions migrated as expected for predominantly dimeric and trimeric protein preparations. These data demonstrate that substantial amounts of trimeric and dimeric R2gp140, sufficient in quantity for use as immunogen, can be produced and stored by this technology.

It should be understood that the foregoing discussion and examples merely present a detailed description of certain preferred embodiments. It therefore should be apparent to those of ordinary skill in the art that various modifications and equivalents can be made without departing from the spirit and scope of the invention. All journal articles, other references, patents, and patent applications that are identified in this patent application are incorporated by reference in their entirety.

Example 4

Materials and Methods. The soluble oligomeric R2gp140 glycoproteins are produced by expression in stable HEK293T cell line cultures under reduced (optiMEM, Invitrogen) serum conditions. The proteins are purified sequentially using lentil lectin affinity chromatography, Capto-DEAE adsorption, and final separation by size-exclusion chromatography using a Superdex-200 prep grade gel filtration column. Three versions of R2gp140 oligomer are shown (FIG. 10), all have the cleavage sites mutated. WT: wild-type truncated gp140; +GCN: gp140 appended with the GCN4 trimerization domain at the C-terminus; +linker-GCN: gp140 with a 15aa flexible linker in place of the cleavage site between gp120 and gp41 ectodomain and appended with the GCN4 trimerization domain at the C-terminus 3 ug of each purified protein is loaded in each lane. Panel A (FIG. 10): samples are treated with reducing SDS-PAGE sample buffer, boiled and separated by SDS-PAGE and stained with coomassie. Panel B (FIG. 10): samples are treated and separated using 3-12% Blue Native PAGE (Invitrogen).

Figures 10A, 10B:
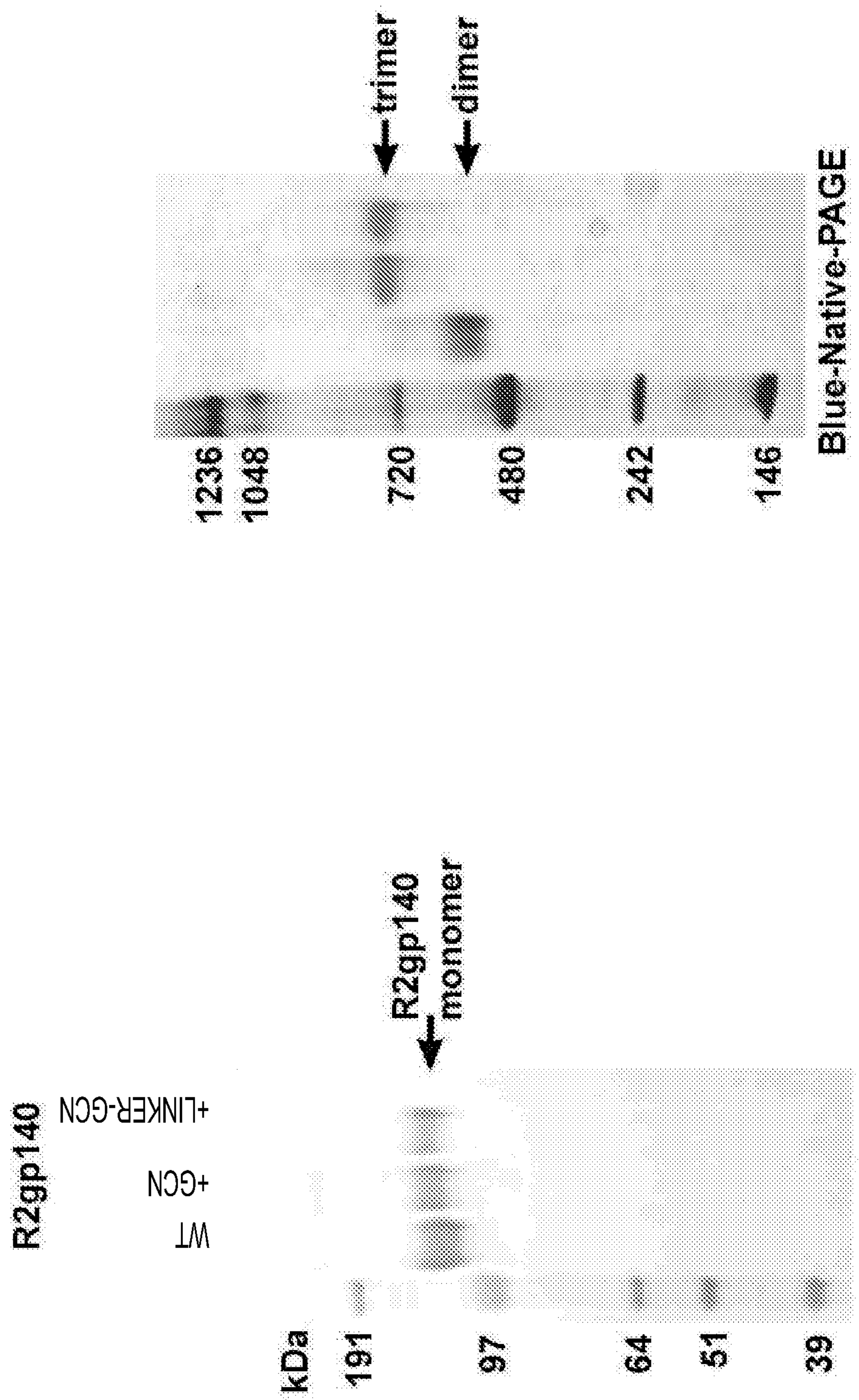
FIG. 10 shows the analysis of wild-type (WT) R2g140, R2gp140-GCN (trimer) and R2gp140-linker-GCN (trimer with flexible linker) following final purification and pooling of individual fractions. Panel A shows each protein sample under SDS-reduced conditions and Panel B shows an identical amount of material analyzed by Blue Native PAGE. Both the R2gp140-GCN and R2gp140-linker-GCN migrate as a trimer with a MW ~720 kDa; whereas the wild-type R2gp140 is primarily dimeric and can be purified as >90% pure dimer and migrates as a dimer with a MW of ~520 kDa.

Results. Both the R2gp140-GCN and R2gp140-linker-GCN migrate as a trimer with a MW ~720 kDa; whereas the wild-type R2gp140 is primarily dimeric and can be purified as >90% pure dimer and migrates as a dimer with a MW of ~520 kDa (FIG. 10).

Example 5

Materials and Methods. Each type of R2gp140 protein, (WT) R2g140, R2gp140-GCN (trimer) and R2gp140-linker-GCN (trimer with flexible linker) was analyzed using a panel of monoclonal antibodies as well as binding competence for CD4. In order to gauge quality of the R2gp140 preparation, the purified R2gp140 preparations were examined for CD4 binding competence and reactivity to panels of monoclonal antibodies (mAbs) including both conformation-dependent and independent mabs as well as particular mAbs known to react to R2gp140 and demonstrating a particular profile (CD4i) mabs. R2gp140 oligomer exhibits a unique ability to be recognized by CD4i mabs both with and without CD4 binding, whereas other gp140 strains require CD4 binding in order for CD4i mAbs to bind to gp140 (Env).

Results. Shown in FIG. 11 is specific mAb binding assessed by precipitation followed by Western blot detection (IP-Western assay). The left side of FIG. 11 demonstrates the characteristic binding reactivity to a panel of CD4i specific human mAbs and with a CD4-gp120 epitope complex specific mAb. The mAb binding assay to the R2gp140s is performed both with and without complex formation with CD4 assayed by IP-Western blot. The mAb 12CA5 is an HA epitope tag specific antibody (control). As we have previously observed, the binding of CD4 appears not required for efficient interaction of any of these antibodies with Panel A: R2g140 (wild-type); Panel B: R2gp140-GCN (trimer); and Panel C: R2gp140-linker-GCN (trimer with flexible linker), indicating that these epitopes are pre-exposed on the R2gp140 oligomers regardless of whether CD4 receptor is pre-bound to the protein (FIG. 11). CG10 mAb reactivity is completely dependent on CD4 binding to the proteins. Thus, the binding reactivity of R2gp140 to this panel of CD4i mAbs is a unique property and no other HIV-1 envelope glycoprotein has been reported to have similar properties.

Shown on the right side of FIG. 11 is the direct binding reactivity of several murine and human mAbs. D19 is a conformation independent V3-loop specific murine antibody. D38.1, D40, D54 and D10 are conformation-dependent gp41 specific murine mAbs. 2G12 is a well-characterized gp120-glycan-specific human mAb and 4E10 and 2F5 are well-characterized gp41 reactive human mAbs. The wild-type R2gp140 protein which contains a mixture of dimer and trimer oligomers (90% dimer) possesses weaker binding or presentation of the epitopes recognized by 4E10, 2F5 and D38.1. Whereas, and of significance, both the stabilized purified R2gp140 trimer (both with and without the flexible linker exhibits significant improvement in the binding of these mAbs, with the R2gp140-linker-GCN exhibiting the most improved binding characteristics. This improvement may translate into a better vaccine immunogen when used in vivo and could elicit the important types of neutralizing antibody responses represented by the 4E10 and 2F5 epitopes.

What is claimed:

1. A fusion polypeptide capable of inducing production of a cross-reactive neutralizing anti-serum against multiple strains of HIV-1 comprising a first polypeptide and a second polypeptide, wherein the first polypeptide comprises SEQ ID NO: 2, and wherein the second polypeptide comprises a trimerization domain.

2. The fusion polypeptide of claim 1, wherein the second polypeptide comprises SEQ ID NO: 6.

3. The fusion polypeptide of claim 1, wherein the fusion polypeptide is capable of forming a trimer.

4. An oligomer polypeptide comprising the fusion polypeptide of claim 1.

5. The oligomer polypeptide of claim 4, wherein the oligomer is a trimer.

6. The oligomer polypeptide of claim 4, wherein the oligomer polypeptide comprises homologous fusion polypeptides.

7. The fusion polypeptide of claim 1, wherein the fusion polypeptide further comprises a third polypeptide.

8. The fusion polypeptide of claim 7, wherein the third polypeptide comprises a polypeptide cleavage site.

9. The fusion polypeptide of claim 1, wherein the fusion polypeptide comprises at least one linker sequence.

10. An immunogenic composition comprising the fusion polypeptide of claim 1, and a pharmaceutically acceptable carrier.

11. The immunogenic composition of claim 10, further comprising an adjuvant.

* * * * *